US006287758B1

(12) United States Patent
Okun et al.

(10) Patent No.: US 6,287,758 B1
(45) Date of Patent: Sep. 11, 2001

(54) METHODS OF REGISTERING TRANS-MEMBRANE ELECTRIC POTENTIALS

(75) Inventors: Ilya Okun; Alex Okun; Gregory Kaler, all of San Diego, CA (US)

(73) Assignee: Axiom Biotechnologies, Inc., San Diego, CA (US)

( * ) Notice: Subject to any disclaimer, the term of this patent is extended or adjusted under 35 U.S.C. 154(b) by 0 days.

(21) Appl. No.: 09/535,261

(22) Filed: Mar. 23, 2000

(51) Int. Cl.[7] .................................................. C12Q 1/68
(52) U.S. Cl. .................... 435/4; 435/4; 435/6; 435/91.1; 435/91.2; 436/86; 436/87; 436/88; 436/164; 436/166; 436/172; 436/175; 436/177; 422/61
(58) Field of Search .................................. 435/4, 6, 91.1, 435/91.2; 436/86, 87, 88, 164, 166, 172, 175, 177; 422/61

(56) References Cited

U.S. PATENT DOCUMENTS

| | | |
|---|---|---|
| 5,611,035 | 3/1997 | Hall . |
| 5,616,502 * | 4/1997 | Haugland et al. ...................... 436/86 |
| 5,804,436 | 9/1998 | Okun et al. . |
| 5,919,646 | 7/1999 | Okun et al. . |
| 5,955,604 * | 9/1999 | Tsien et al. ........................... 540/222 |
| 6,001,579 * | 12/1999 | Still et al. .............................. 435/7.1 |

OTHER PUBLICATIONS

Bammel, et al., "The interaction of potential–sensitive molecular probes with dimyristoylphosphatidylcholine vesicales investigated by $^{31}$P–NMR and electron microscopy," *Biochim. Biophys. Acta* 896:136–152 (1987).
Brauner, et al., "Comparative measurements of membrane potentials with microelectrodes and voltage–sensitive dyes," *Biochim. Biophys. Acta.* 771:208–216 (1984).
Bunting, et al., Fluorescent cationic probes of mitochondria, *Biophys. J.* 56:979–993 (1989).
Cabrini, et al., "Potential–Sensitive Response Mechanism of DiS–C$_3$–(5) in Biological Membranes," *J. Membr. Biol.* 92:171–182 (1986).
Epps, et al., "Characterization of the steady–state and dynamic fluorescence properties of the potential–sensitive dye . . . , " *Chem. Phys. Lipids* 69:137–150 (1994).
Flewelling, et al., "Hydrophobic ion interactions with membranes, Thermodynamic Analysis of Tetraphenylphosphonium Binding to Vesicles," *Biophys. J.* 49:531–540 (1986).
Flewelling, et al., "The Membrane Dipole Potential In a Total Membrane Potential Model, Applications to Hydrophobic Ion Interactions with Membranes," *Biophys. J.* 49:541–552 (1986).
Franklin, et al., "Probes of membrane electrostatics: synthesis and voltage–dependant partitioning of negative hydrophobic ion spin labels in lipid vesicles," *Biophys. J.* 64:642–653 (1993).
Gonzalez, et al., "Voltage Sensing by Fluorescence Resonance Energy Transfer in Single Cells," *Biophys J.* 69:1272–1280 (1995).

Gonzalez, et al., "Improved indicators of cell membrane potential that use fluorescence resonance energy transfer," *Chem. Biol.* 4:269–277 (1997).
Guillet, et al., "DiO–C$_3$–(5) and DiS–C$_3$–(5): Interactions with RBC, Ghosts and Phospholipid Vesicles," *J. Membrane Biol.* 59:1–11 (1981).
Salvador, et al., "Ca$^{2+}$Transport by Reconstituted Synaptosomal ATPase Is Associated with H$^+$ Countertransport and Net Charge Displacement," *J. Biol. Chem.* 273:18230–18234 (1998).
Sims, et al., "Studies on the mechanism by which Cyanine Dyes Measure Membrane Potential in Red Blood Cells and Phosphatidylcholine Vesicles," *Biochemistry* 13:3315–3330 (1974).
Smith, et al., "Kinetics of the Potential–Sensitive Extrinsic Probe Oxonol VI in Beef Heart Submitochondrial Particles," *J. Membrane Biol.* 46:255–282 (1979).
Dunne, J.F., "Time Window Analysis and Sorting," *Cytometry* 12:597–601 (1991).
Ransom, et al., "AT$_1$ Angiotensin Receptors Mobilize Intracellular Calcium in a Subclone of NG108–15 Neuroblastoma Cells," *J. of Neurochem.* 58:1883–1888 (1992).
Ransom, et al., "Flow Cytometric Analysis of Internal Calcium Mobilization via a B$_2$–Bradykinin Receptor on a Subclone of PC–12 Cells," *J. of Neurochem.* 56: 983–989 (1991).
Ransom, et al., "Flow Cytometric Selection of Responsive Subclones and Fluorimetric Analysis of Intracellular Ca$^{2+}$ Mobilization," *Molecular Imaging in Neuroscience: A Practical Approach* pp. 209–233 (1994).
Ransom, et al., "Flow Cytometric Systems for Drug Discovery and Development," *Optical Diagnostics of Living Cells III* D.L. Farkas and R.C. Lief eds. Proceedings of SPIE, vol. 3921, pp. 90–100 (2000).
Ransom, et al., "Isolation of Sublones With Enhanced Ca$^{2+}$ Response Homogeneity by Flow Cytometric Selection of Single Cells During a Ligand–Activated Ca$^{2+}$ Response," *Methods: A Companion to Methods in Enzymology* 2(3):227–233 (1991).

* cited by examiner

Primary Examiner—W. Gary Jones
Assistant Examiner—Janell E. Taylor
(74) Attorney, Agent, or Firm—Knobbe, Martens, Olson & Bear, LLP

(57) ABSTRACT

Sensitive methods for identifying compounds having biological activity comprising combining living cells with two fluorescent membrane permeable ionic dyes having the same charge sign, the first of which has an emission spectrum which overlaps the excitation spectrum of the second fluorescent membrane penetrative dye. The fluorescence is then induced by illuminating the dyes at a wavelength corresponding to the excitation spectrum of the first fluorescent dye and emission is then registered at a wavelength corresponding to the emission spectrum of the second fluorescent dye (FRET). The change in the FRET is indicative of a modulation of cell membrane potential by the biologically active compounds.

41 Claims, 20 Drawing Sheets

WAVELENGTH, nm

METHODS OF REGISTERING TRANS-MEMBRANE ELECTRIC POTENTIALS

FIELD OF THE INVENTION

The present invention relates to the field of cell biology, more particularly to measuring electric potentials across cell plasma and mitochondrial membranes.

BACKGROUND OF THE INVENTION

The existence of an electric potential across cell membranes, such as plasma membranes or the mitochondria, is a major factor in proper cell functioning. Excitatory cells, including neurons or muscle cells, actively separate negatively charged molecules inside the cell from positively charged ones in the space outside the membrane. This charge distribution maintains a steady-state homeostasis transmembrane electric potential that is characteristic for resting cells. Upon cell activation, either with an electric field or with specific signal transducing molecules, the resting membrane potential changes. This change causes a cell reaction, which leads to, for example, neuronal signal propagation or muscular contraction.

The ability to monitor the cell membrane potential in single cells or in cell populations is important for understanding both the intricate molecular mechanisms underlying cell functioning, as well as for drug development. Two main approaches have been developed to monitor cell membrane potentials: direct electrical measurements with microelectrodes and indirect measurement of membrane potential by following the redistribution of specially developed lipophilic ions labeled with either an isotope or a fluorescent moiety.

Both membrane permeable probes and non-membrane-permeable probes are used to monitor cell membrane potentials. Permeable fluorescent probes usually have high sensitivity to membrane potential changes but are very slow to respond to these changes. Non-permeable probes usually react quickly to membrane potential changes but have very low sensitivity. The main disadvantage of these probes is that their fluorescence intensity changes upon membrane depolarization or hyperpolarization. An approach based on fluorescence intensity can be confounded by variations in dye loading, cell density, or variability in excitation intensity. Also, it can be misleading when one considers the use of compounds with inherent spectral characteristics that interfere with the fluorescence of a probe.

As an example of membrane permeable probes, the class of negatively charged oxonols is best suited for measuring plasma membrane potentials because they are excluded from entering mitochondria due to the high negative charge inside the mitochondria. The oxonols are represented by a family of structures with the following general formulas (1 and 2):

FORMULA 1:

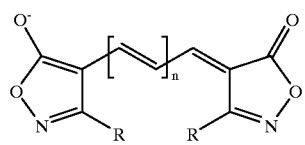

-continued

FORMULA 2:

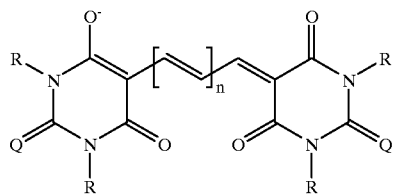

In these formulas, Q is either O or S and each R is independently chosen from an alkyl or aryl group of 1 to 20 carbon atoms. These compounds are commercially available through various sources including Molecular Probes, Inc. (Eugene, Oreg.).

The bis-isoxazolone oxonols of Formula 1, namely Oxonol V and Oxonol VI (FIG. 2), have been used for measuring membrane potentials mainly by absorption rather than fluorescence [Salvador et al., *J. Biol. Chem.* 273:18230–18234, 1998; Smith et al., *J. Memb. Biol.* 46:255–282, 1979] (incorporated herein by reference). The bis-barbituric acid oxonols of formula 2 are used for monitoring predominantly plasma membrane by changes in fluorescence intensity upon cell membrane depolarization or hyperpolarization [Epps et al., *Chem. Phys. Lipids* 69:137–150, 1994; Brauner et al., *Biochim. Biophys. Acta.* 771:208–216, 1984] (incorporated herein by reference).

Another class of widely used membrane permeable dyes comprises carbocyanine derivatives of the following general Formula 3:

FORMULA 3:

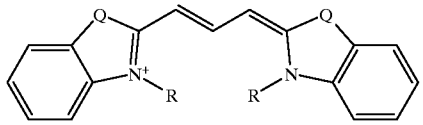

In this formula, Q is O, S or $C(CH_3)_2$ and each R is independently an alkyl group of 1 to 20 carbon atoms. These dyes, Indo- (DiI), thia- (DiS) and oxa- (DiO) carbocyanines with R ranging from one to seven carbon atoms, were the first potential sensitive probes developed [Sims et al., *Biochemistry* 13:3315–3330, 1974] (incorporated herein by reference). These molecules, being positively charged, concentrate on the surface and inside the plasma membrane [Cabrini et al., *J. Membr. Biol.* 92:171–182, 1986] (incorporated herein by reference) and mitochondria [Bunting et al., supra.] (incorporated herein by reference), where they aggregate with subsequent quenching of the fluorescence. This fluorescence intensity decrease is caused by potential-dependent binding of the molecules onto the membrane and aggregate formation [Guillet et al., supra.] (incorporated herein by reference). The main parameter used to monitor membrane potential in intact cells is the fluorescence intensity of dye in water, non-quenched phase of the dye. In this case it makes it impossible to distinguish between membrane potential changes of plasma membrane from that of mitochondria since an overall intensity for the cells is measured.

Alternative approaches have been developed [U.S. Pat. No. 5,661,035; Gonzalez et al., *Chem. Biol.* 4:269–277, 1997; Gonzalez et al., *Biophys. J.* 69:1272–1280, 1995] (incorporated herein by reference) that utilize Fluorescence Resonance Energy Transfer (FRET) phenomenon that can register membrane potentials in a ratiometric manner. These approaches and the matter compositions offered to practice FRET can elicit fast responses with high sensitivity to membrane potential changes. Unfortunately, these approaches and compositions are likely to cause artificial alterations in membrane structure and as a consequence, in cell functional behavior due to the unnatural incorporation of the highly hydrophobic dyes into the cell membrane. Additionally, use of fluorescently labeled lectin (WGA) as an affinity anchor for the second energy transfer counterpart reagent, can provoke cell functional responses by itself.

SUMMARY OF THE INVENTION

The present invention provides improved compounds and methods for measuring cell membrane electrical potential. In particular, the present invention uses donor and acceptor molecules to provide a fluorescent signal that is both rapid and sensitive to changes in membrane potential.

One embodiment of the present invention is a method for identifying compounds having biological activity comprising combining living cells with a first membrane penetrative dye and with a second membrane penetrative dye to form a test cell mixture; combining the test cell mixture with a test compound to form a test cell/compound mixture; placing said test cell/compound mixture into a detection zone; and measuring a cellular response in said test cell. Preferably, the biological activity is an initiation of the cellular response. Advantageously, the biological activity is a block of the cellular response In one aspect of this preferred embodiment, the cellular response is measured by a change in plasma membrane electric potential of the cells. Preferably, the cells are in a suspension. Alternatively, the cells are adhered to a substrate. In another aspect of this preferred embodiment, the substrate is beads, a microscope slide or a well of a multi-well plate. Preferably, the test compound is in solution. In one aspect of this preferred embodiment, the test compound solution comprises a standard compound having known biological effect. Preferably, the standard compound is an ion channel opener, ion channel blocker, ion transporter blocker or ion pump blockers. Advantageously, the plasma membrane electric potential is measured by fluorescence energy transfer between the first membrane penetrative dye and the second membrane penetrative dye. Preferably, the first dye is a fluorescent lipophilic anion having a characteristic excitation maximum between about 300 nm and 800 nm. Advantageously, the second dye is a fluorescent lipophilic anionic molecule having a characteristic excitation maximum which overlaps with the emission spectrum of the first dye. In one aspect of this preferred embodiment, the second dye has a characteristic excitation maximum of between about 220 nm and 700 nm. Preferably, the test cell/compound mixture is contacted with light having a wavelength corresponding to the excitation spectrum of the first membrane penetrative dye, and the fluorescence intensity of the test cell/compound mixture is registered at a wavelength corresponding to the emission spectrum of the second membrane penetrative dye. Advantageously, the fluorescence intensity obtained on the test cell/compound mixture in the presence of the test compound is compared to the fluorescence intensity obtained on the test cell in the absence of the test compound. In one aspect of this preferred embodiment, the fluorescence intensity obtained on the test cell/compound mixture in the presence of a standard compound having a known cellular effect is compared to the fluorescence intensity obtained on the test cell in the absence of the standard compound. Preferably, the fluorescence intensity obtained from the test cell/compound mixture with the test compound and a standard compound having a known cellular effect is compared to the fluorescence intensity obtained on the test cell/compound mixture with the standard compound. Advantageously, the fluorescence emission intensity obtained on the test cell/compound mixture with the test compound is compared to the fluorescence emission intensity obtained on the test cell/compound mixture with the test compound and at least one standard compound having a known biological effect. A change in the fluorescence intensity indicates that the compound has an initiating effect on the cellular response, and a change in said fluorescence intensity indicates that the standard compound exerts the known biological response. The diminishing of the known effect induced by the standard compound in the presence of the test compound indicates that the test compound is an antagonist. The diminishing of the known effect induced by the test compound in the presence of the standard compound indicates that the test compound is an agonist.

The present invention also provides a method for identifying compounds having biological activity comprising: combining living cells with a membrane penetrative dye to form a test cell mixture; combining the test cell mixture with a test compound to form a test cell/compound mixture; placing the test cell/compound mixture into a detection zone; and measuring a cellular response. Preferably, the biological activity is exerted through modification of plasma membrane electric potential of the cells. Advantageously, the biological activity is exerted through modification of mitochondrial membrane electric potential of the cells. Preferably, the cells are in a suspension. Alternatively, the cells are adhered to a substrate. The substrate is preferably beads, a microscope slide or a well of a multi-well plate. Advantageously, the test compound is in a solution. In one aspect of this preferred embodiment, the test compound solution comprises a standard compound having a known biological effect. Preferably, the standard compound is an ion channel opener, ion channel blocker, ion transporter blocker or ion pump blocker. Preferably, the test compound solution comprises a mixture of at least one test compound and at least one standard compound. In one aspect of this preferred embodiment, the cellular response is measured by change in electric potential across a membrane. Preferably, the membrane is the plasma membrane. Alternatively, the membrane is the mitochondrial membrane. In one aspect of this preferred embodiment, the membrane penetrative dye is a fluorescent lipophilic cation chosen from a group of fluorescent dyes whose spectral characteristics are different when in solution and when bound to the cell membranes. In one aspect of this preferred embodiment, the change in electric potential is measured by a change in fluorescence intensity of a membrane penetrative dye measured at least at two excitation and at least at two emission wavelengths. Preferably, at least one excitation and at least one emission wavelength is chosen from the set of wavelengths characteristic of aqueous form of the dye. In one aspect of this preferred embodiment, at least one excitation and at least one emission wavelength is chosen from the set of wavelengths characteristic of the membrane bound form of the dye. Advantageously, a change in ratio of fluorescence intensity measured at excitation and emission wavelengths characteristic of water soluble form of the dye to fluorescence intensity at excitation and emission wavelengths characteristic of the membrane bound form of the dye is indicative of both plasma membrane and mitochondrial membrane electric potential changes. A decrease in the ratio is indicative of plasma membrane depolarization, and an increase in the ratio is indicative of mitochondrial membrane depolarization.

DETAILED DESCRIPTION OF THE INVENTION

The present invention provides methods for use in generating electric potential sensitive ratiometric changes in fluorescence of dyes in living cells or cell populations. In a preferred embodiment, the methods are used to identify compounds having biological activity, including initiation or blocking of cellular responses. In another preferred embodiment, the cellular response is measured by a change in plasma membrane electric potential of cells or cell lines. The cells and cell lines used with the method of the present invention may be prokaryotic or eukaryotic, and derived from plants, mammals and invertebrates, preferably humans. In one embodiment, the membrane potential sensor system comprises a first dye, which is preferably a membrane permeable fluorescent ion capable of redistributing between the cell cytoplasm and outer media upon changes in the membrane potential in accordance with its electrochemical potential, and a second dye, which is preferably a second penetrable fluorescent ion, preferably with the same charge sign as the first dye. The dyes are selected in such a way that one dye can be a donor and another reagent an acceptor of the light energy for fluorescence resonance energy transfer (FRET) to take place. When the cell has a resting potential of −60 mV across its plasma membrane (minus inside), the penetrable ion theoretically can have a 10-fold concentration gradient between external and internal water volumes. The same concentration gradient will exist across the cell membrane. When the membrane is depolarized, the penetrable ions redistribute evenly between the two membrane surfaces and the concentration of the fluorophore ions on the inside surface of the membrane increases. The potential sensitive fluorescent signal is created by fluorescence energy transfer between two neighboring molecules of the FRET pair. It is should be apparent to a person skilled in the art that the efficiency of the FRET is greatly dependent on the concentration of the interacting molecules and when the membrane is depolarized, the energy transfer between the donor and acceptor will increase as a product of the concentration of the dyes.

Figure 1:
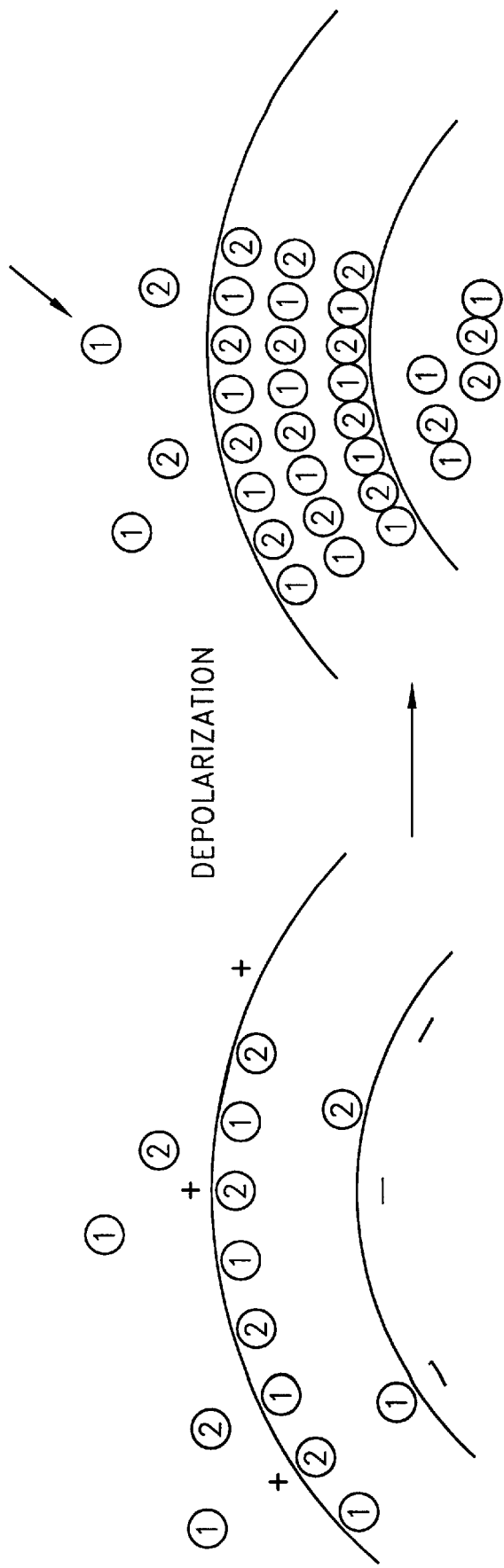
FIG. 1 schematically shows the redistribution of the negatively charged lipophilic dyes upon membrane depolarization that enhances fluorescence resonance energy transfer (FRET).
Figure 2A:
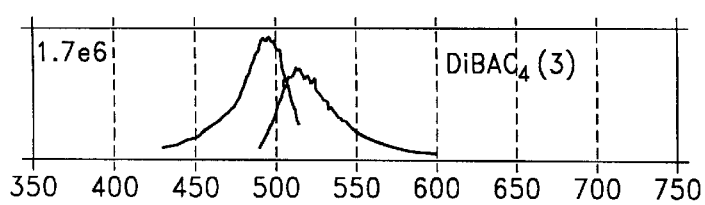
FIG. 2 shows the chemical structure, excitation spectra and emission spectra for a series of oxonol dyes.
Figure 2A:
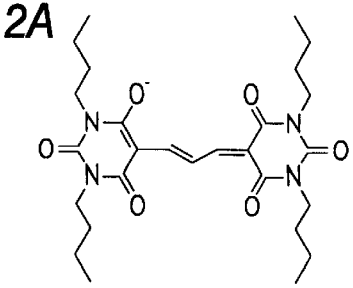
Figure 2B:
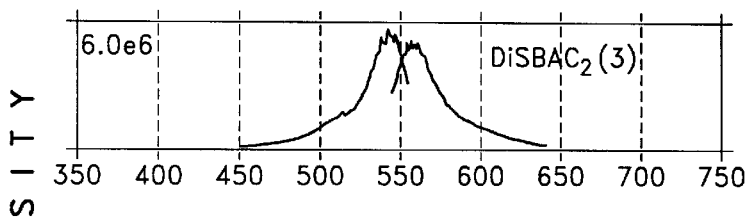
Figure 2B:
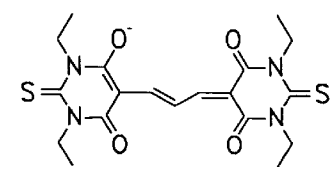
Figure 2C:
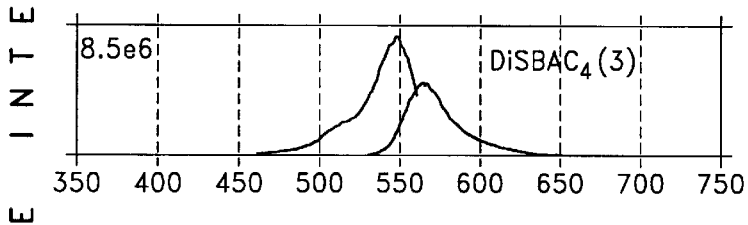
Figure 2C:
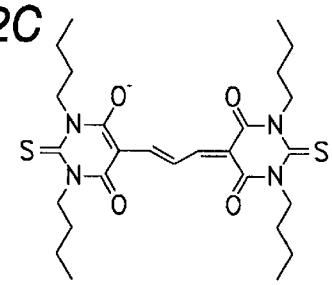
Figure 2D:
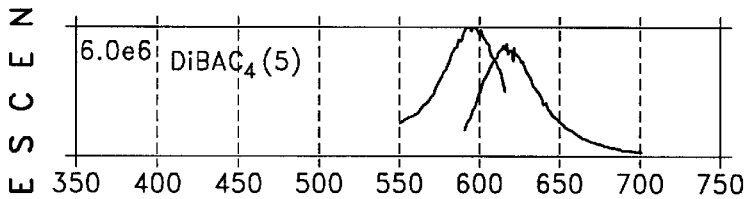
Figure 2D:
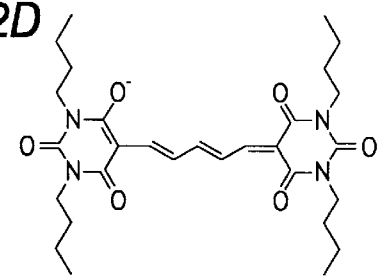
Figure 2E:
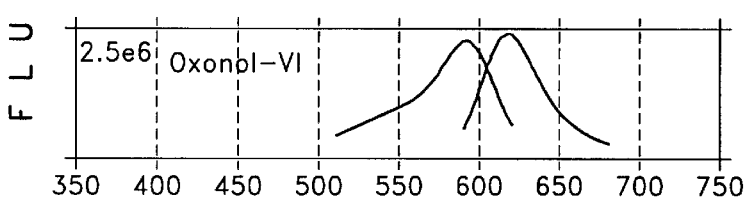
Figure 2E:
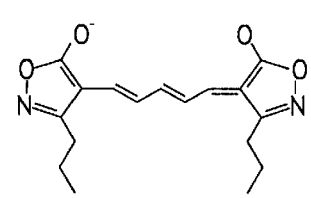
Figure 2F:
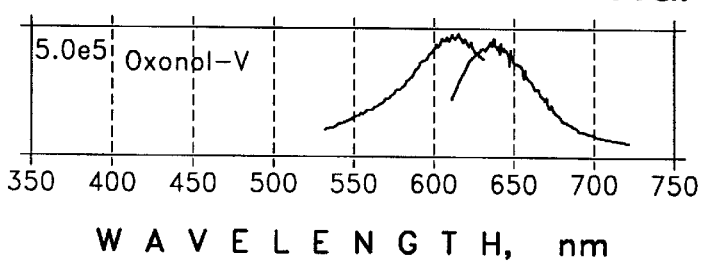
Figure 2F:
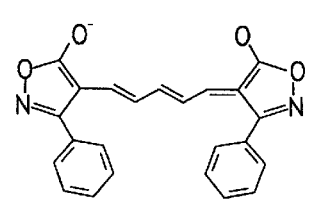

More specifically, the present invention provides methods for use in generating electric potential sensitive ratiometric changes in fluorescence of dyes in single cells or cell populations. One method of the present invention comprises combining an energy acceptor dye and an energy donor dye with cells, irradiating the cells with light having a wavelength characteristic of the absorption spectra of the energy donor, and measuring fluorescence emission at two wavelengths characteristic of the emission spectra of the energy donor and the energy acceptor. The first dye is preferably a membrane penetrable fluorescent ion, preferably a lipophilic fluorescent ion, which redistributes between the outer and inner volumes of the cell upon changes in membrane potential in accordance with its electro-chemical potential. This first fluorescent dye is considered an energy acceptor. In a preferred embodiment, the first fluorescent dye has a characteristic excitation maximum between about 300 and 800 nm. The second reagent, considered to be the energy donor, is also a membrane penetrable fluorescent ion, preferably lipophilic, and preferably with the same charge sign as the first fluorescent dye, to perform energy transfer to the first dye. In a preferred embodiment, the second fluorescent dye has a characteristic excitation maximum between about 220 and 700 nm. The schematic of the interaction between the probes in a membrane and generation of the electric potential sensitive signal is shown in FIG. 1. The resting potential of the cells has a negative charge localized inside; therefore, negatively charged probe molecules, represented here by members of the oxonol family of lipophilic fluorescent anions, are expelled from the cells and have a higher concentration in the media surrounding the cells compared to the intracellular concentration. A dye concentration gradient also exists across the membrane with a high concentration of the molecules in the outer leaflet and low concentration in the inner leaflet of the membrane. When the membrane is depolarized, the molecules located in the outer leaflet will move to the inner leaflet, and will be replaced from outside the cell with new molecules coming from the water space surrounding the cell. The total concentration of the molecules in the membrane will rapidly increase. Because of the increased concentration of both donor and acceptor molecules in the membrane, FRET occurs efficiently and produces a greatly enhanced signal in comparison to the signal associated with a polarized membrane.

For measuring predominantly plasmalemma membrane potentials, the use of lipophilic anions is preferable to cations for several reasons. First, the highly negative potential in mitochondria prevents anions from entry and accumulation in the mitochondrial matrix. Second, lipophilic anions have better membrane penetrability than cations [Flewelling et al., *Biophys. J.* 49:531–540, 1986] (incorporated herein by reference) and can concentrate better in the plasma membrane due to negative binding enthalpy compared to the positive (repulsive) binding enthalpy characteristic for cations [Flewelling et al., *Biophys. J.* 49:541–552, 1986] (incorporated herein by reference). Finally, they do not show significant disturbance of the membrane lipid bilayer [Bammel, *Biochim. Biophys. Acta.* 896:136–152, 1987] (incorporated herein by reference). It has also been shown that the lipophilic anions not only have stronger membrane binding but also have faster transmembrane migration rate compared with the positive hydrophobic cations [Franklin et al., *Biophys J.* 64:642–653, 1993] (incorporated herein by reference).

In a preferred embodiment of the invention, both fluorescent ions are anions. When the cell membrane is polarized, it has a negative charge localized inside the cell and positive charge localized outside the cell. The intracellular negative charge prevents anionic reagents from entering into the cell, creating a concentration gradient of these reagents across the cell membrane. The concentration of the reagents is chosen in such a way that there is no energy transfer between them in the extracellular fluid. Upon depolarization, both reagents penetrate into the intracellular volume and their concentration in the cell membrane increases so that energy transfer between donor and acceptor molecules takes place. Because FRET is a bimolecular event, its efficiency will increase as a product of concentrations of the two dyes. Thus, if the concentrations of the two dyes are equal, then energy transfer efficacy would increase as the square of the dye concentration increase. In other words, two fold increases in dye concentration would cause a four fold increase in FRET efficiency. This type of non-linear dependency on the change in dye concentrations during membrane depolarization significantly augments the sensitivity of the method. The energy transfer that occurs between the two dye molecules, donor and acceptor, in the plasma membrane can be monitored by the change in the fluorescence intensity of the acceptor molecule while exciting the donor molecule with the wavelength that is not absorbed by the acceptor molecule.

One skilled in the art will readily appreciate that the pair of donor-acceptor dyes for sensing membrane potential can be composed of pair of any negatively charged lipophilic molecules, with an energy donor and energy acceptor spectral characteristics fulfilling fluorescence energy transfer criteria. To fulfill this criteria the donor has to have an emission spectra overlapping with the absorption spectra of an acceptor molecule. The acceptor is also a negatively charged lipophilic anion with emission spectra shifted to the red compared to the donor emission spectra, so that its fluorescence intensity could be spectrally separated from the donor emission spectra and measured readily. The structures and excitation-emission spectra for a series of six exemplary oxonols, $DiSBAC_2(3)$, $DiSBAC_4(3)$, $DiBAC_4(3)$, $DiBAC_4(5)$, Oxonol V, and Oxonol VI, are presented in FIG. 2.

Of course, oxonols suitable for use in the present invention as FRET sensors are not limited to the examples presented in FIG. 2. For this series of oxonols presented, or for any other fluorescent molecules, a person skilled in the art can appreciate that different combinations of potential sensor pairs can be used which have overlapping emission and excitation spectra. Such sensor pairs, whether constituting oxonol dyes or other compounds, are still considered to fall within the scope of the present invention. In a preferred embodiment, the emission spectrum of the donor and excitation spectrum of the acceptor overlap by about 50%, 40%, 30% or 20%, more preferably by about 10% or 5%. Many fluorophores are known in the art or are commercially available from various sources. Donor-acceptor pairs suitable for use in the present invention can be readily determined by measuring excitation and emission spectra using a fluorescence spectrometer and determining whether there is overlap between the two.

For simultaneous measurement of both plasma membrane and mitochondria membrane potentials, lipophilic cations are preferred. The cations, having a positive charge, are redistributed by concentrating in the cytoplasm and in mitochondria corresponding to their relative electric potentials. Thus, three concentrations of the probe are in a steady-state equilibrium with each other: the external concentration (water volume), the cytoplasmic concentration, and the intra-mitochondrial concentration. In accordance with the Nernst equation, each 60 mV of membrane potential brings about 10-fold concentration difference of a permeable ion across the membrane. The plasma membrane potential of excitable cells is about 60 to 120 mV and the membrane potential of mitochondria is about 180 to 240 mV. This creates approximately 10 to 100 fold concentration gradient of the permeable cation across the plasma membrane and 1,000 to 10,000 concentration gradients on the mitochondria membrane. It is well established that upon an increase in concentration, the carbocyanine dyes aggregate and their fluorescence is quenched. Upon depolarization, the dye is redistributed back into the extracellular space and its fluorescence intensity increases. Conventionally, the change in the fluorescence intensity of dye in the outer volume is measured to indicate the level of membrane polarization. These fluorescence intensity changes are identical for depolarization of both plasma membrane and mitochondria and cannot be used to differentiate depolarization events in both of these sites.

In another preferred embodiment, the fluorescence intensity of lipophilic cations, preferably carbocyanine dyes, is measured at two different excitation/emission wavelength pairs, one characteristic of dye in solution and another of dye bound to the cell membrane and other intracellular structures. While the fluorescence intensity at "water" excitation/emission wavelengths allows monitoring changes in the membrane potential of both the plasmalemma and the mitochondria, the fluorescence intensity at "bound" excitation/emission wavelengths monitors predominantly mitochondrial membrane potential. By simultaneously registering the fluorescence intensity at both wavelength pairs, it is possible to distinguish membrane potential changes in both plasmalemma and mitochondria.

In a preferred embodiment, living cells are first incubated with a membrane penetrative dye, or with a suitable combination of fluorescent donor-acceptor dye pairs to form a test cell mixture. A test compound with unknown effect is then added to the above mixture to form a test cell/compound mixture. The mixture is then placed into a detection zone in order to detect/measure a cellular response to the test compound. In a preferred embodiment, the test compound is in solution. The detection zone is where the sample is analyzed by the detection system which may be, for example, a cuvette of a spectrofluorometer, or an optical well in a 96-well plate fluorescence reader. The cellular response, as reflected in a change of plasma membrane electric potential, is preferably measured by fluorescence energy transfer between the first membrane penetrative dye acting as a donor and the second membrane penetrative dye acting as an acceptor. The apparatus described in U.S. Pat. No. 5,804,436, the entire content of which is incorporated herein by reference, for example, can be used to conveniently measure the response. Cells grown in suspension or adhered to a substrate such as a well, preferably the bottom of a well (round or flat) of a multi-well plate may be used. Cells grown on a microscope slide or coated onto beads are also suitable for the analysis in accordance with the present invention. A variety of compounds with known effect on trans-membrane potential can be used as standard compounds, such as openers or blockers of ion channels, blockers of ion transporters or ion pumps.

The modification of electrical potential of the plasma membrane can occur as a result of change in the activity of ion channels such as sodium, potassium, chloride and calcium channels. The change in the activity of voltage operated or chemo-regulated channels can also bring about change in electrical potential of plasma membrane. Ion channels, upon activation, allow for the ions to move across the cell membrane in accordance with their electrochemical potentials. There are two main types of ion channels: voltage operated and ligand-gated. Voltage operated channels are activated to the open state upon changes in transmembrane electric potential. Sodium channels in the neuronal axon or L-type calcium channels in neuromuscular junctions exemplify this kind of channel. Ligand-gated channels are activated to the open state upon binding a certain ligand with the chemoreceptor part of their molecules. The classical example of a ligand-gated channels is the nicotinic cholinergic receptor which, at the same time, is the sodium channel.

Ion transporters represent another group of membrane transport assembly which can affect plasma membrane electrical potential in accordance with the present invention. Ion transporters use the electrochemical energy of transmembrane gradients of one ion species to maintain gradients of other ion counterpart. For example, the $Na+/Ca^{2+}$-exchanger uses the chemical potential of the sodium gradient directed inward to pump out calcium ions against their chemical potential. Other ion transporters include $Na+/Cl^-$, $Ca^{2+}/H^+$, $HPO_4^{2-}$, and the like.

Ion pumps exemplify another category of membrane transport assembly that can modify electrical potential of plasma membrane in accordance with the present invention. Ion pumps act to maintain transmembrane ion gradients utilizing ATP as a source of energy. Ion pumps include, but are not limited to, $Na+/K+$-ATPase for maintaining transmembrane gradient of sodium and potassium ions, $Ca^{2+}$-ATPase for maintaining transmembrane gradient of calcium ions and $H+$-ATPase for maintaining transmembrane gradient of protons.

In another preferred embodiment, trans-membrane electric potential is monitored by a method comprising the steps of: (a) combining a homogeneous suspension of living cells with membrane penetrative sensing dyes to form a cell/dye mixture, (b) combining the cell/dye mixture with a test compound having an unknown cellular effect to form a test mixture, (c) directing the test mixture through a detection zone; and (d) measuring a cellular response of the suspended cells to the test compound as the test mixture is flowing through the detection zone. The method will often include the additional steps of: (e) combining a homogeneous suspension of the cells with a standard compound having a known effect on the cellular response of the cells to form a standard mixture; (f) directing the standard mixture through the detection zone; and (g) measuring the cellular response of the cells to the standard compound. In one embodiment, the standard compound and the test compound are simultaneously mixed with the cells in the combining steps, and the measuring step detects the known effect or an alteration of the known effect. The standard compound can be an agonist or antagonist of the cellular response. In one mode of operation, steps (b), (c) and (d) are performed first, and then steps (e), (f), and (g) are performed using a single suspension of the cells prepared in step (a). In another mode of operation, steps (b) and (e) are performed simultaneously; steps (c) and (f) are performed simultaneously; and steps (d) and (g) are performed simultaneously. If the cellular response is detected in step (d) to indicate that the test compound is active to generate the response, and the standard compound is an antagonist, then a decrease in the cell response from step (d) of the first mode to combined steps (d) and (g) of the second mode, is indicative that the test compound is an agonist of the known effect. If the cellular response is not detected in step (d), indicating that the test compound is not active to generate the response, and the standard compound is an agonist, then an alteration of the known effect detected in step (g) of the first mode as detected in combined steps (d) and (g) of the second mode, is indicative that the test compound is an antagonist of the known effect. Preferably, the method is performed automatically under the direction of a programmable computer on a plurality of test compounds and a plurality of standard compounds, and a successive series of known antagonists is automatically added as the standard compound in step (e) if the cellular response is detected in step (d) to indicate that the test compound is active to generate the cellular response, whereby a decrease in the cellular response detected in combined steps (d) and (g) is indicative that the test compound is an agonist of the known effect; and a series of known agonists is automatically added as the standard compound in step (e) when the cellular response is not detected in step (d), whereby an alteration of the known effect detected in combined steps (d) and (g) is indicative that the test compound is an antagonist of the known effect

EXAMPLE 1

To characterize the spectral compatibility of the anionic lipophilic dyes for exploiting the FRET technique, the excitation and emission spectra were measured in the presence of PC 12 cells (American Type Culture Collection, No. CRL 1721). A suspension of cells in hybridoma medium (Gibco BRL) containing $1.5 \times 10^5$ cells/ml was mixed with the respective dye (final concentration 0.5 µM) for 30 min in a dark container. After the incubation, 3 ml of the suspension was transferred into a rectangular cuvette (1×1×4 cm) and the excitation and emission spectra were recorded using a FluoroMax-2 fluorometer (Instruments SA). The results are shown in FIG. 2.

Figure 3A:
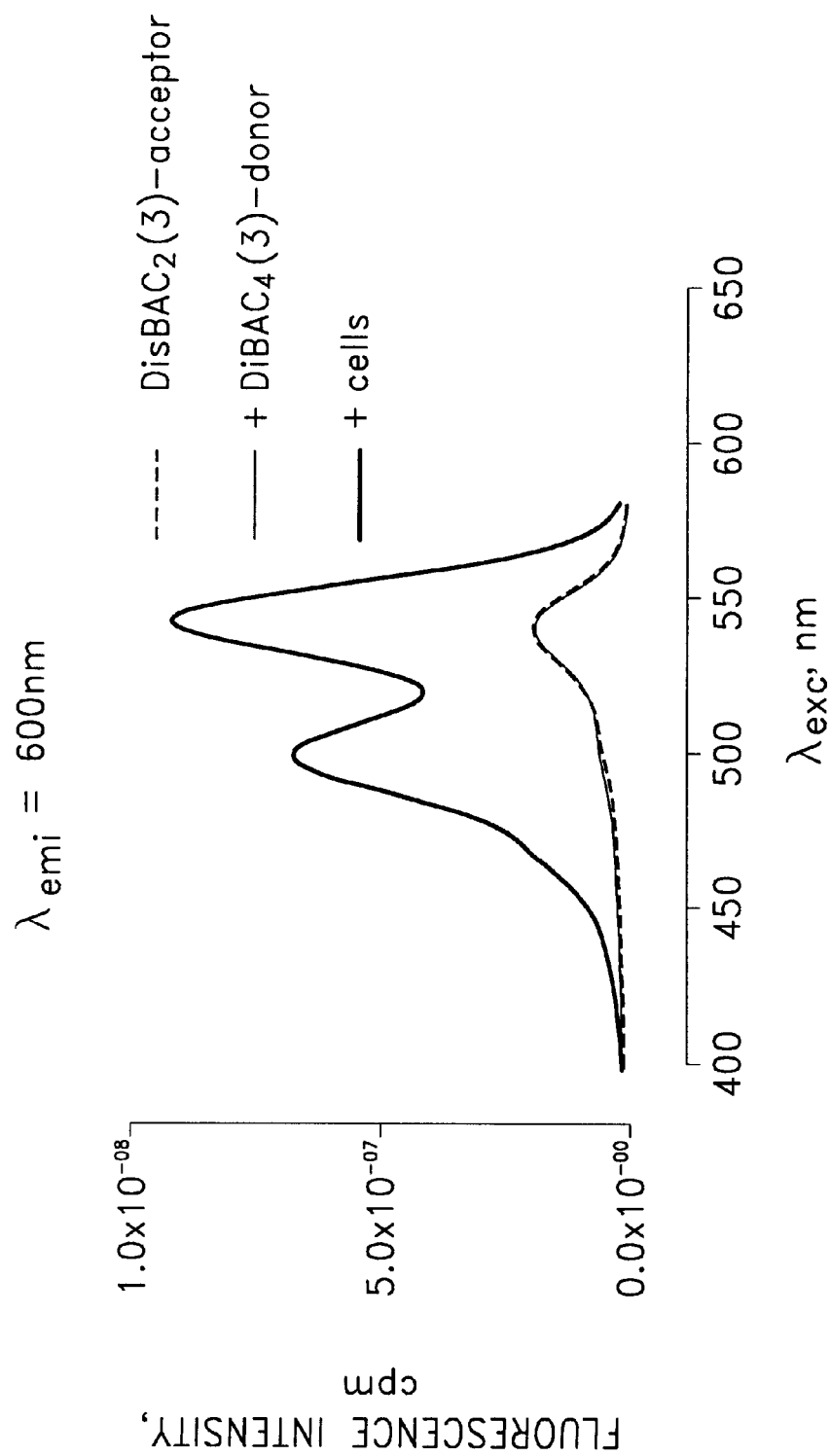
FIGS. 3a–3e show excitation spectra for mixtures of donor and acceptor dyes measured at an emission wavelength characteristic for acceptor dye. $2.5 \times 10^5$ cells/ml were used. The dye concentrations were 500 nM.
Figure 3B:
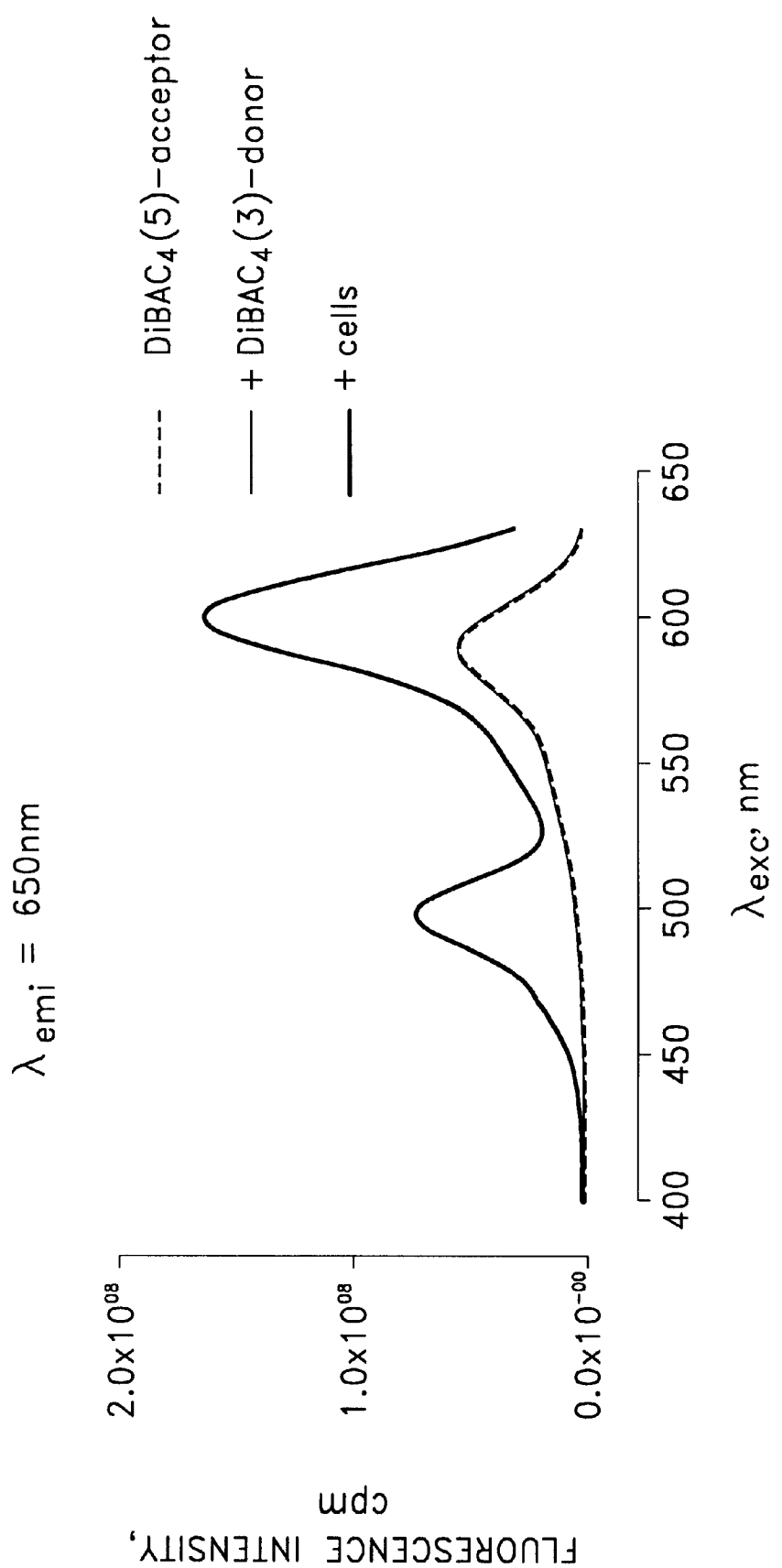
Figure 3C:
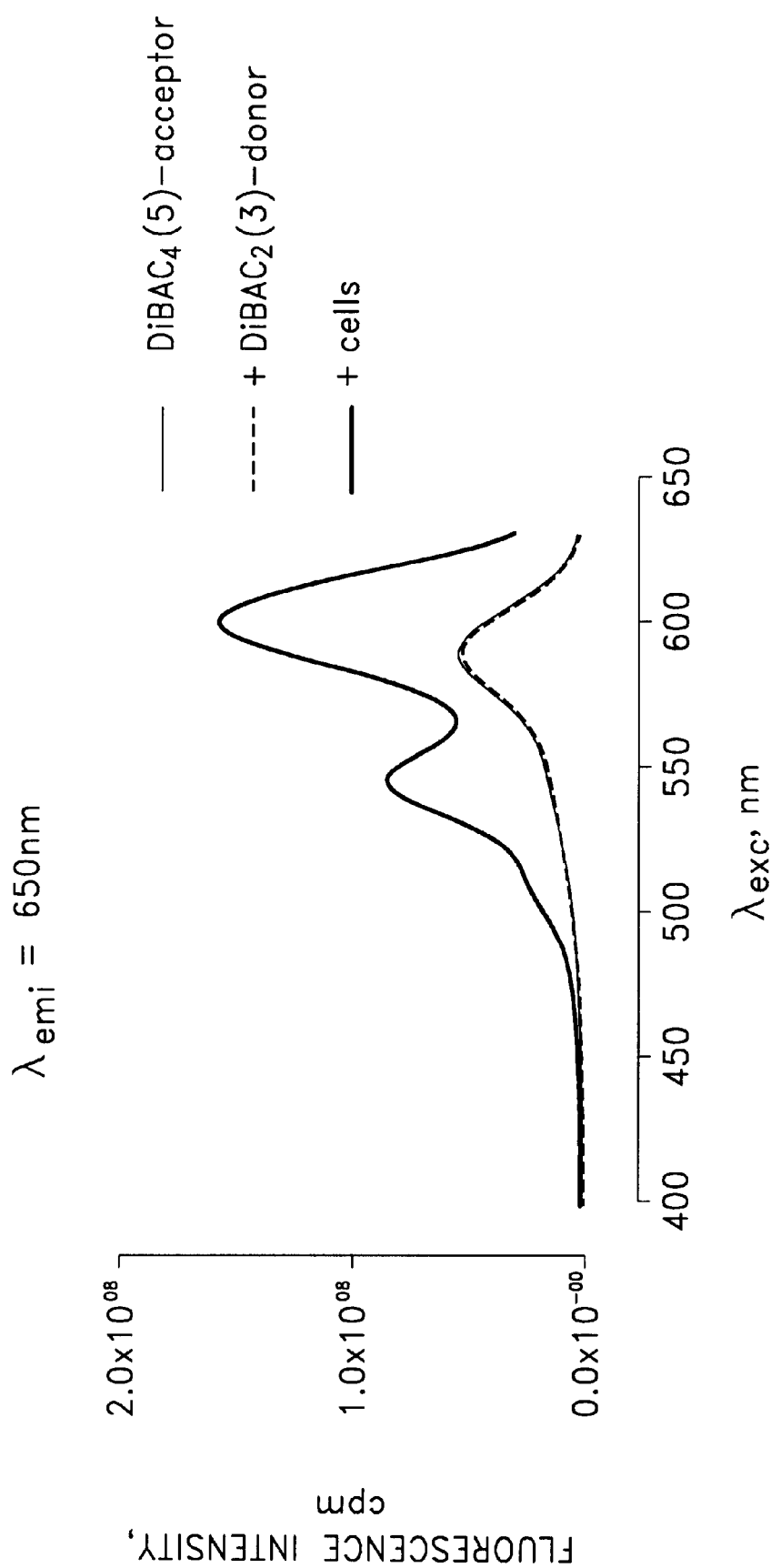
Figure 3D:
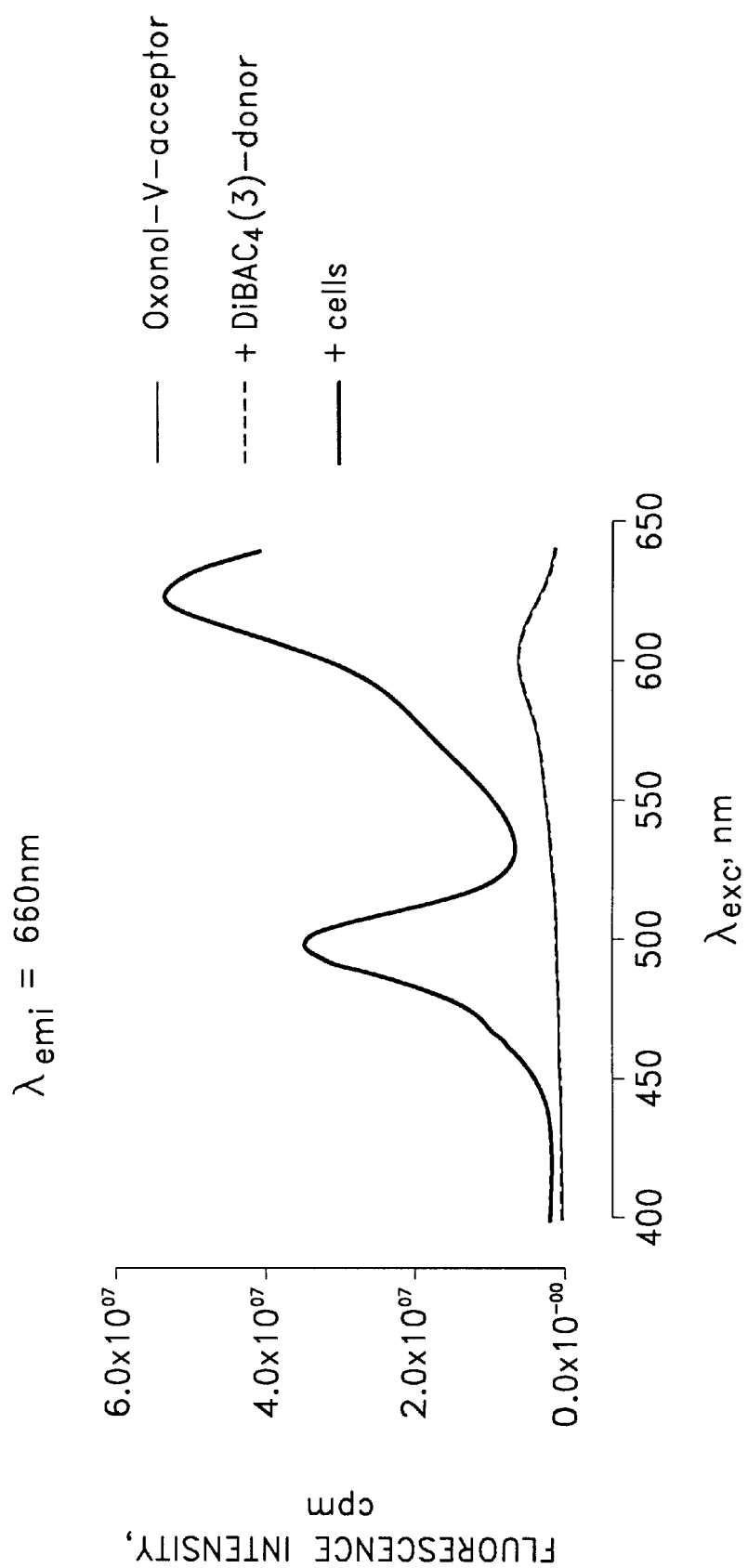
Figure 3E:
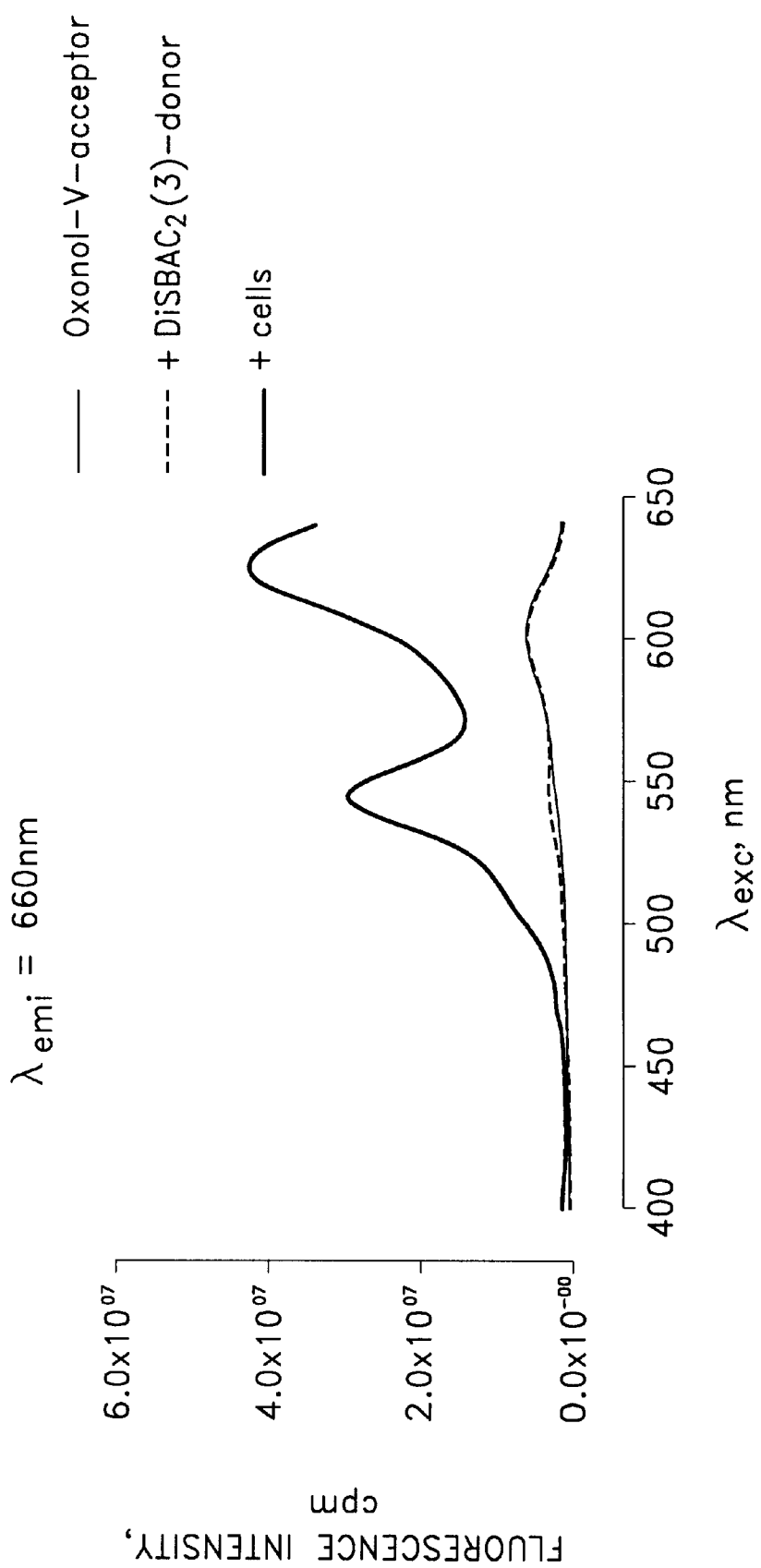

As can be readily appreciated by one skilled in the art, a variety of dye combinations with energy donor and acceptor compatibility can be construed from the dyes shown in FIG. 2, but not so limited. FIG. 3 presents excitation spectra for several donor/acceptor pairs registered either in PBS buffer or in PBS buffer in the presence of PC12 cells ($2.5 \times 10^5$ cells/ml). All dyes were used at a concentration of 0.5 µM. FIG. 3a shows excitation spectra registered at 600 nm for $DiBAC_4(3)$ as the energy donor and $DiSBAC_2(3)$ as the energy acceptor. FIGS. 3b and 3c show excitation spectra registered at 650 nm for $DiBAC_4(3)$ and $DiSBAC_2(3)$, respectively, as the energy donors and $DiBAC_4(5)$ as the energy acceptor. FIGS. 3d and 3e show excitation spectra registered at 660 nm for $DiBAC_4(3)$ and $DiSBAC2(3)$, respectively, as the energy donors and Oxonol-V as the energy acceptor. For all the pairs presented, the emission wavelengths are chosen from the data presented in FIG. 2 in such a way that there is preferably no emission of the donor molecule.

Those skilled in the art can readily appreciate that excitation spectra of the dyes in buffer show only one maximum characteristic for the excitation of the acceptor molecule. Upon cell addition, the intensity of the fluorescence increases and a second maximum appears, which is characteristic for the excitation of corresponding donor molecule. The appearance of the "donor" maximum at the emission wavelength where donor does not emit light, reflects the occurrence of the FRET when cells are present.

EXAMPLE 2

Figure 4A:
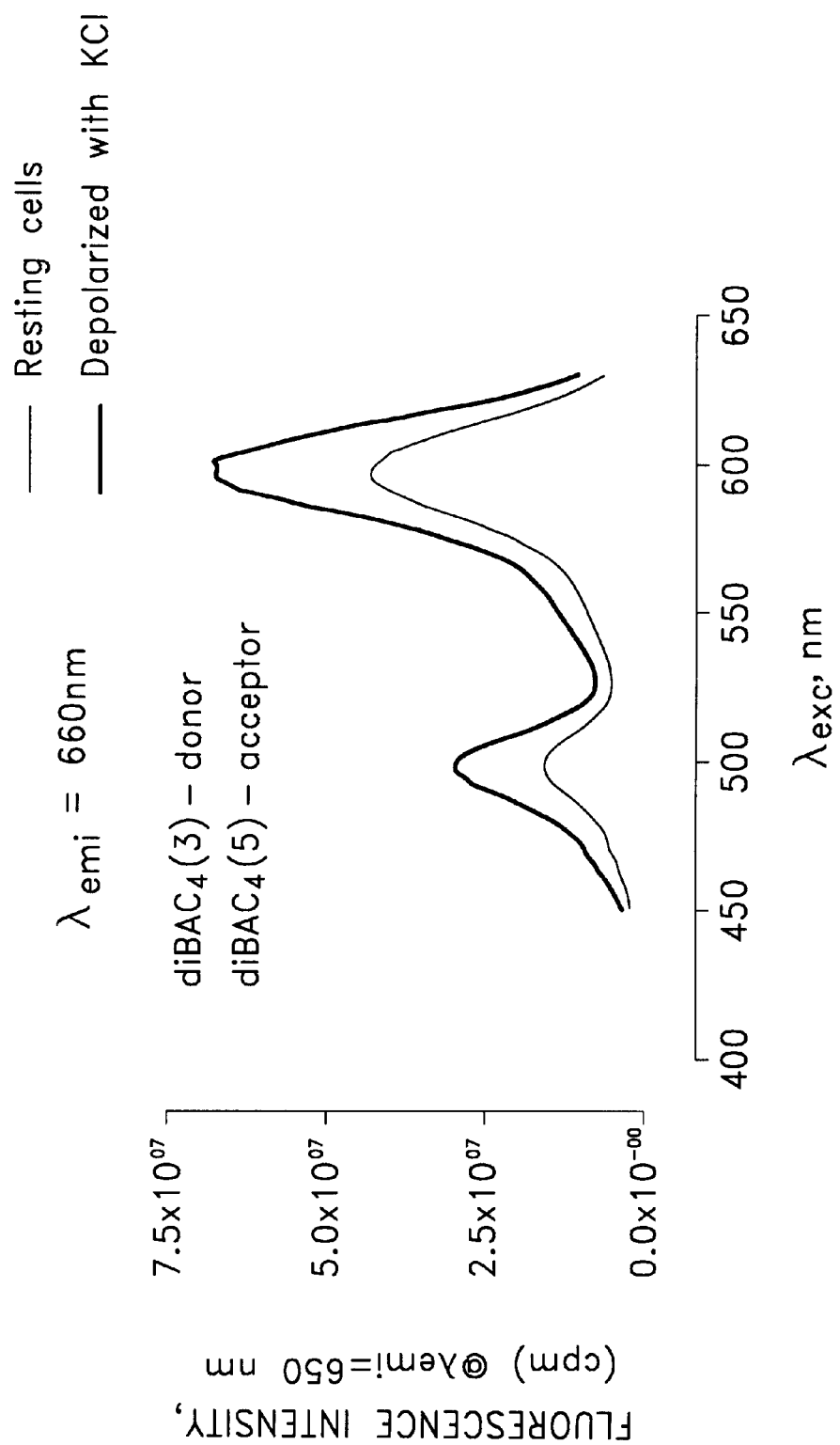
FIGS. 4a–4b show excitation spectra of donor acceptor pairs in resting cells and in cells depolarized with KCl (FIG. 4a) and ratio excitation spectrum (FIG. 4b).
Figure 4B:
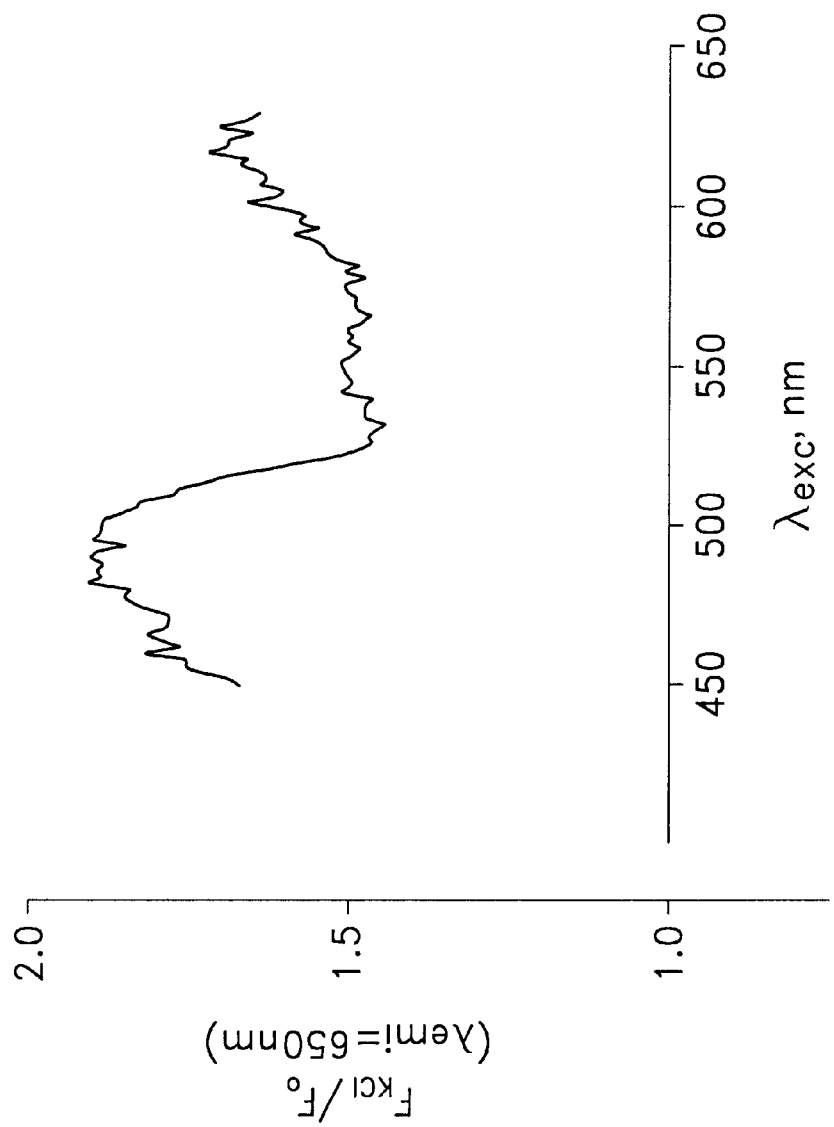

FIG. 4a represents excitation spectra measured at 650 nm, for the pair $DiBAC_4(3)/DiBAC_4(5)$ (donor/acceptor) in the PC12 cell suspension in the presence and in the absence of 50 mM KCl, which is known to depolarize the cells. Cell membrane depolarization leads to additional increase of both fluorescence intensity of the acceptor molecule itself (peak at 600 nm) as well as FRET intensity (peak at 500 nm). After dividing the spectra of cells depolarized with KCl into the spectra of normal cells, represented in FIG. 4b, the increase in the FRET intensity was more pronounced (reaching a two-fold increase) than the increase in the fluorescence intensity of the dye itself. In another set of experiments, an uncoupler of oxidative phosphorylation, DNC, was added to the cells to depolarize mitochondria membrane. The spectral ratio (FIG. 4b) did not show any increase in the fluorescence intensity or in the FRET at any wavelength. This experiment shows that with the anionic lipophilic dyes, the FRET technique can monitor changes exclusively in plasmalemma membrane potential and is not obscured by changes in the mitochondria membrane potential changes.

EXAMPLE 3

Figure 5:
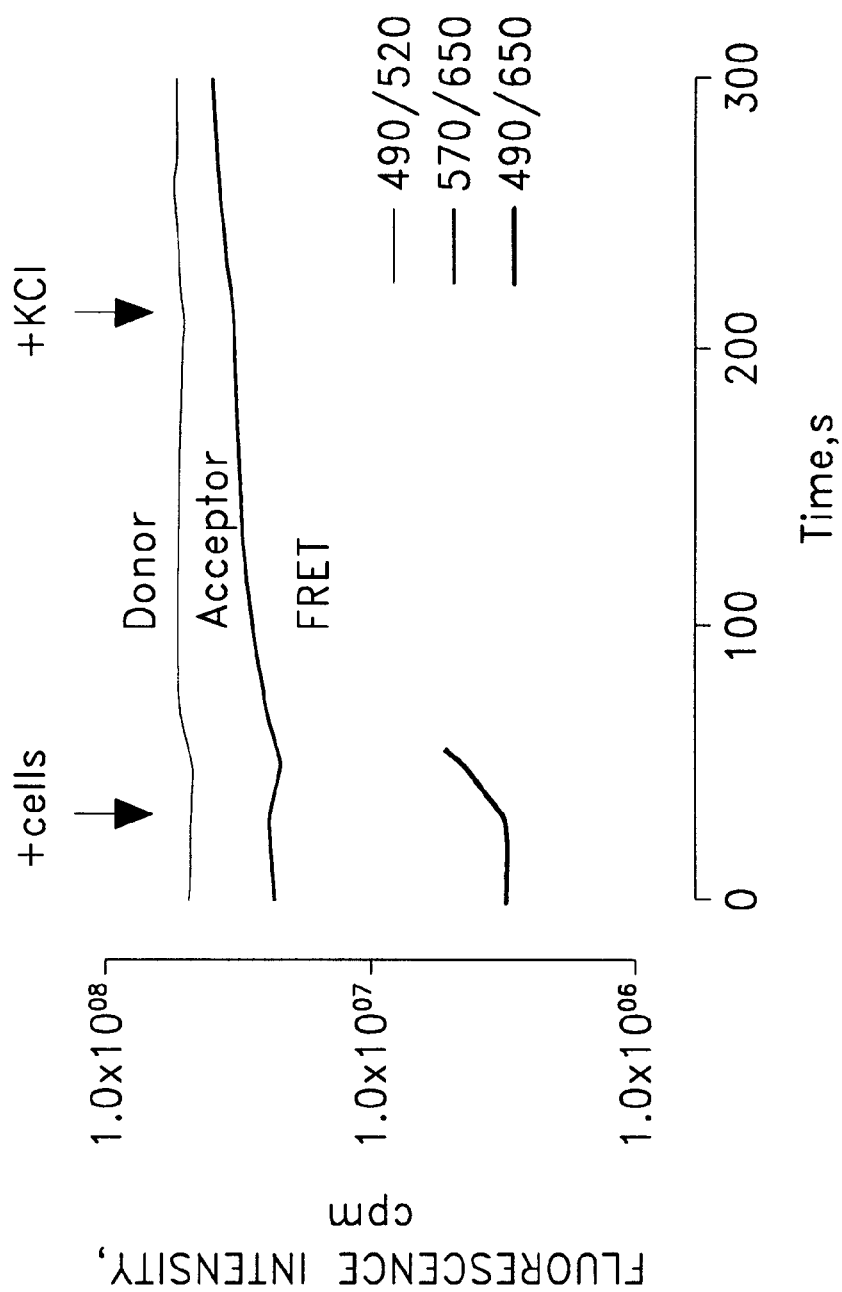
FIG. 5 shows time dependent changes in fluorescence of individual dyes and FRET signal upon addition of PC 12 cells and KCl.

FIG. 5 illustrates $K^+$ induced time dependent changes in the PC12 cell membrane potential which were registered using the donor/acceptor pair, $DiBAC_4(3)/DiBAC_4(5)$. Cells were added to the solution of the two dyes and then a solution of KCl was added to provide a final dye concentration of 50 mM. Changes in fluorescence intensities of individual dyes ($\lambda_{ex}$=490 nm and $\lambda_{em}$=520 nm for $DiBAC_4$(3) and $_{ex}$=570 nm and $_{em}$=650 nm for $DiBAC_4$(5)) as well as intensity of FRET ($\lambda_{ex}$=490 nm and $\lambda_{em}$=650 nm) were constantly monitored. Both dyes responded to the addition of cells and their subsequent depolarization with potassium chloride by increasing the corresponding fluorescence intensity. An important advantage of the present method is that the FRET-based signal intensity ($490_{ex}/650_{em}$) is significantly more sensitive in detecting the presence of cells and cell membrane depolarization than by detection of the intensities of individual dyes.

EXAMPLE 4

Figure 6:
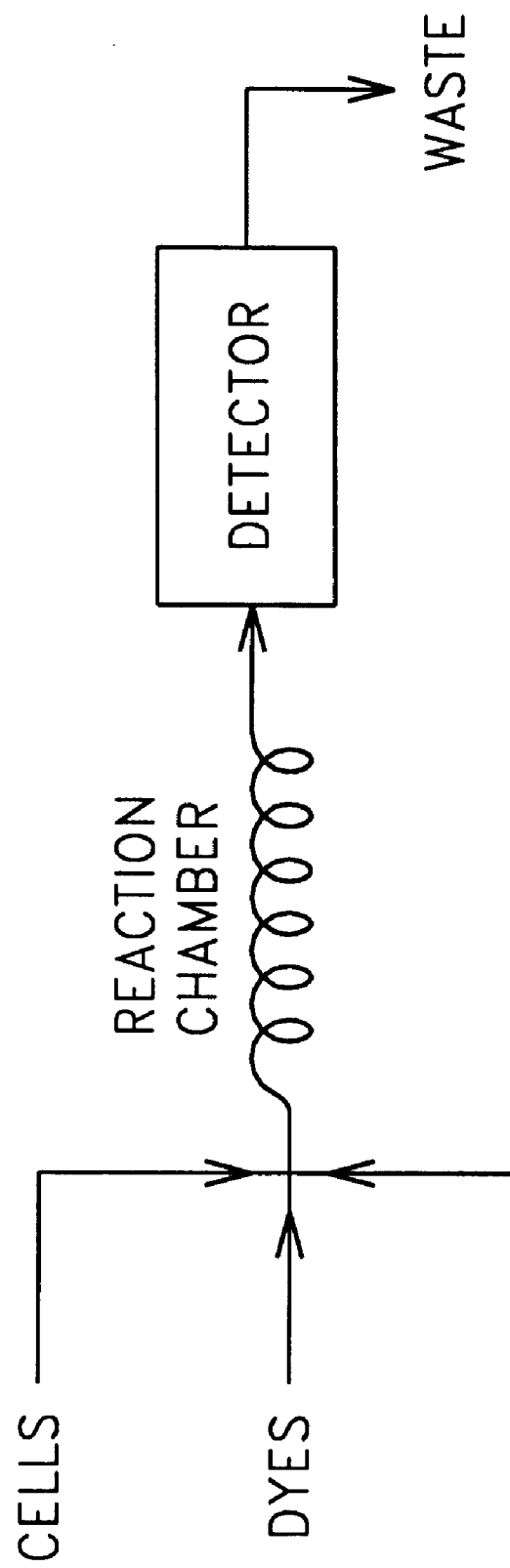
FIG. 6 is a block-diagram of a flow-through device for registering dose-dependent changes in FRET.

The HT-PS 100 system described in U.S. Pat. Nos. 5,804,436 and 5,919,646, the entire contents of which are incorporated herein by reference, was used to register concentration dependent changes in plasmalemma membrane potential upon gradual addition of adenosinetriphosphate, ATP, to the PC12 cells. In the HT-PS 100 system, cells in the hybridoma media (600,000 cells/ml), solution of dyes in PBS (0.5 μM each) and solution of ATP in PBS (20 mM) are constantly mixed together in a flow. The components are mixed in a volumetric proportion of 1:1:1, the concentration of the ATP being changed exponentially during the registration time. The flow diagram of the system's fluidics is shown in FIG. 6. After the three reagent components are combined together, the resulting mixture flows through reaction chamber to allow development of the membrane potential changes to occur. With this set-up, the time between the cell activation with the ATP and registration of the membrane potential is always constant at any ATP concentration (60 seconds).

Figure 7A:
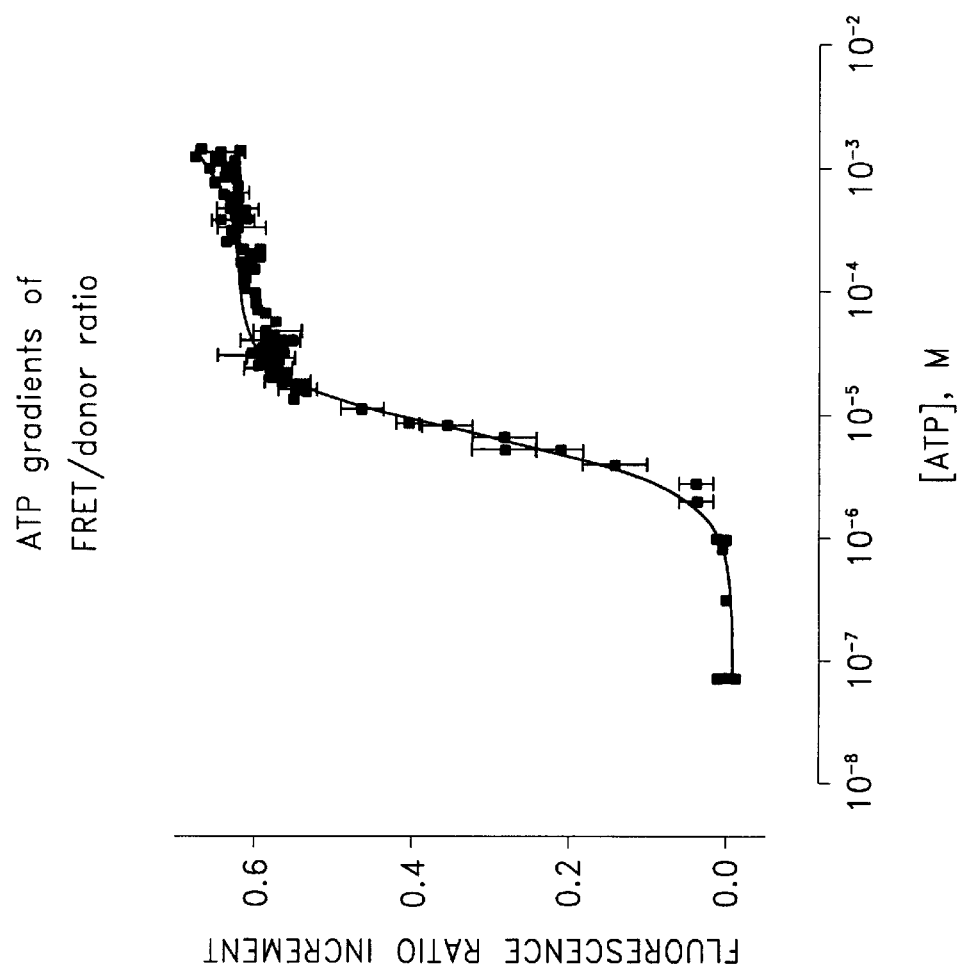
FIGS. 7a–7b show dose-dependent changes in FRET with ATP as an agonist (FIG. 7a) and with KCl as a depolarizing agent (FIG. 7b).
Figure 7B:
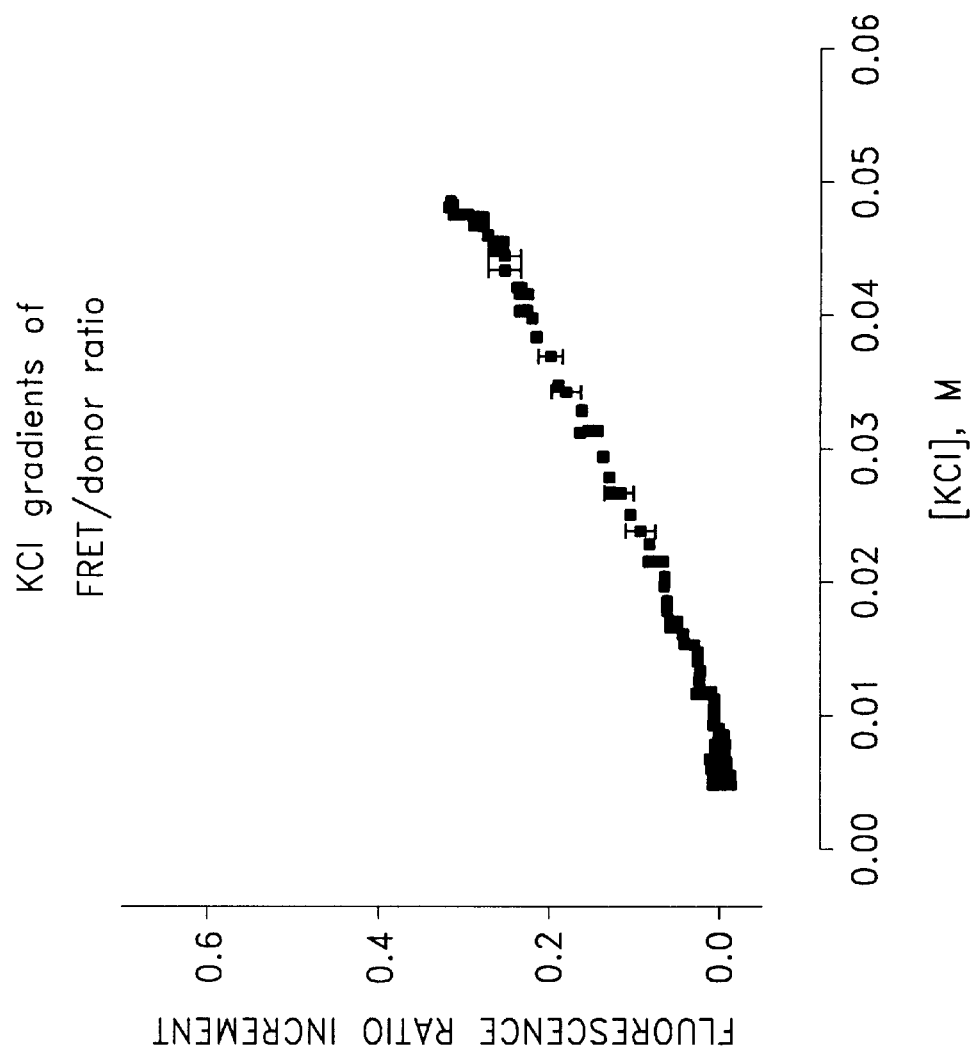

FIG. 7 represents triplicate measurements of dose dependent ATP (A) and potassium (B) induced changes in the plasma membrane potential of the PC12 cells registered by FRET using the $DiBAC_4(3)/DiBAC_4(5)$ dye combination as the donor/acceptor pair. ATP causes saturation type of the membrane depolarization with its concentration, characteristic of binding to the limited number of receptor sites. In contrast, the potassium effect is non-saturable in nature, as is characteristic of the potassium diffusion potential. This approach is very sensitive and allows measurement of physiologically relevant changes in plasma membrane potentials with high precision, with the signal/noise ratio being equal to 110 in these experiments.

EXAMPLE 5

Figure 8A:
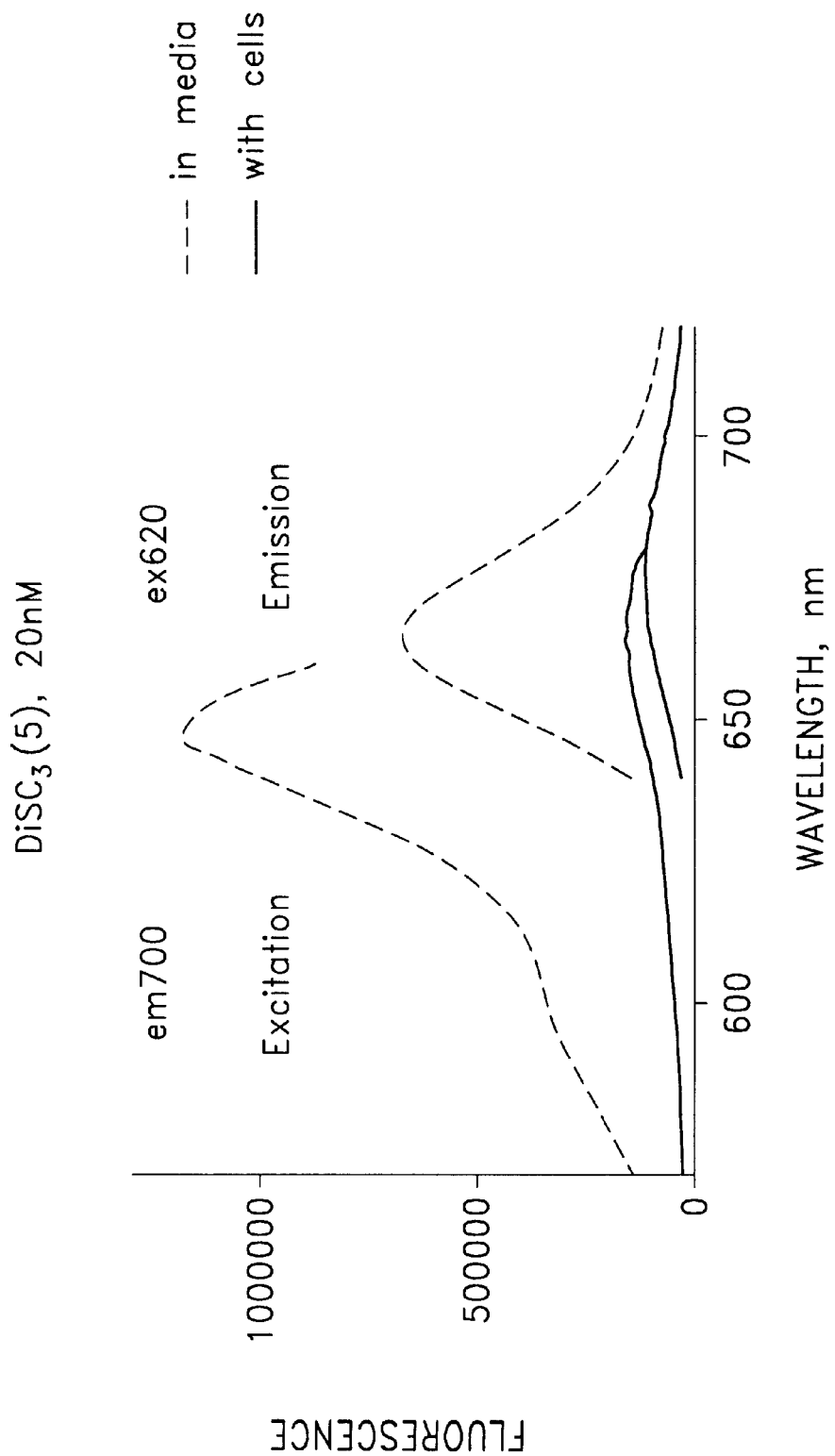
FIGS. 8a–8f show excitation and emission spectra of $DiSC_3(5)$ at different dye to PC12 cell concentration ratios.
Figure 8B:
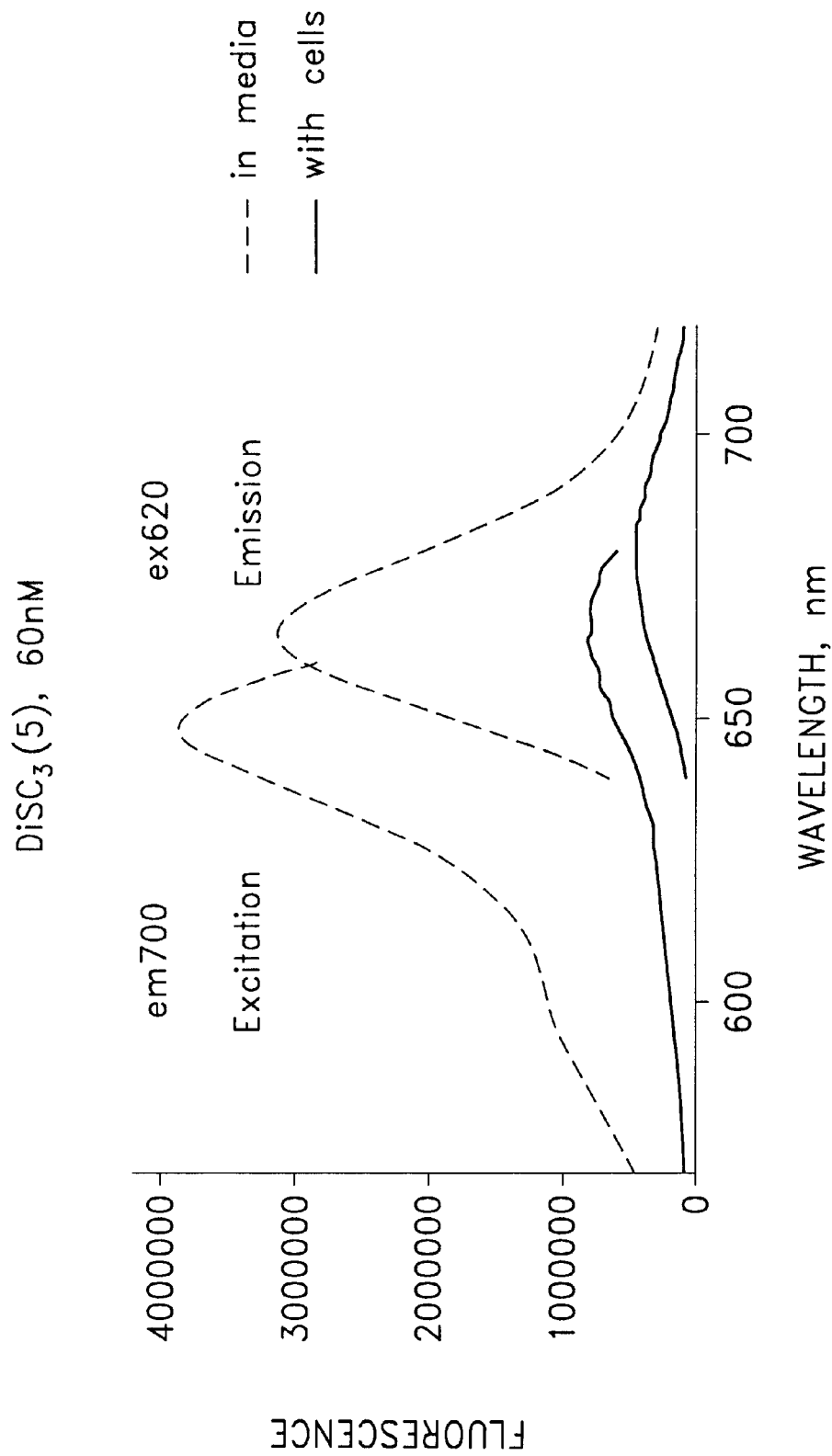
Figure 8C:
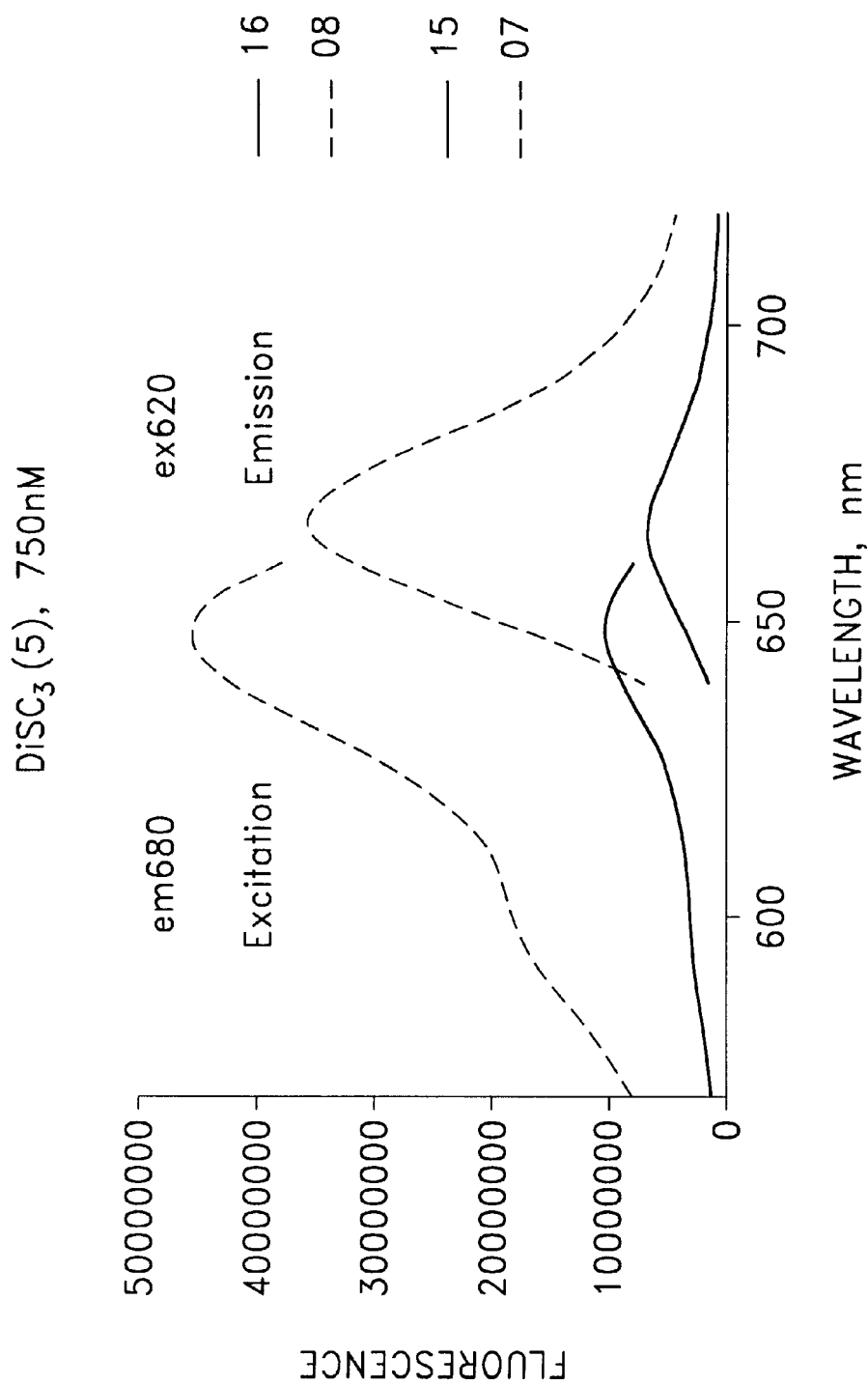
Figure 8D:
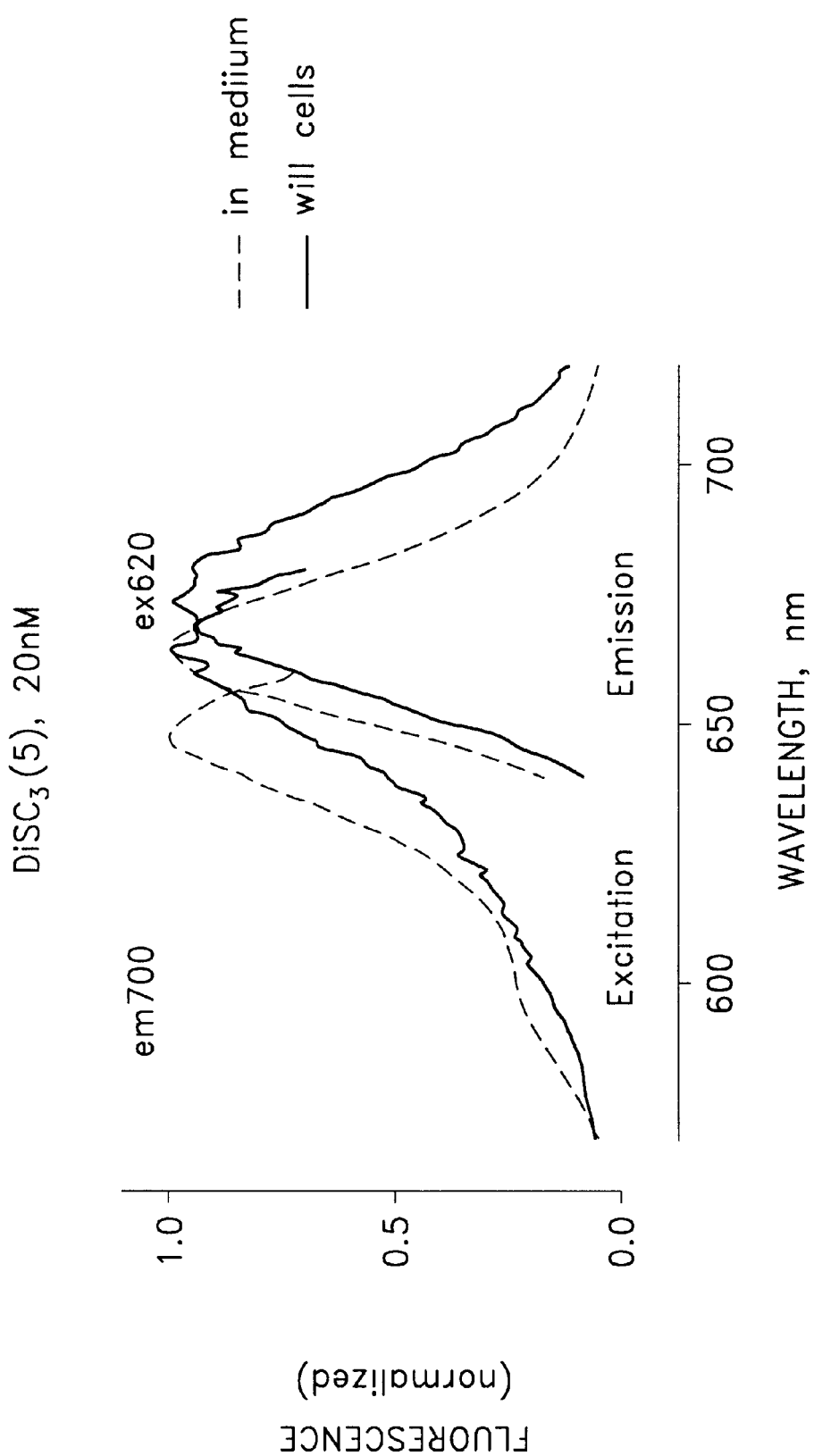
Figure 8E:
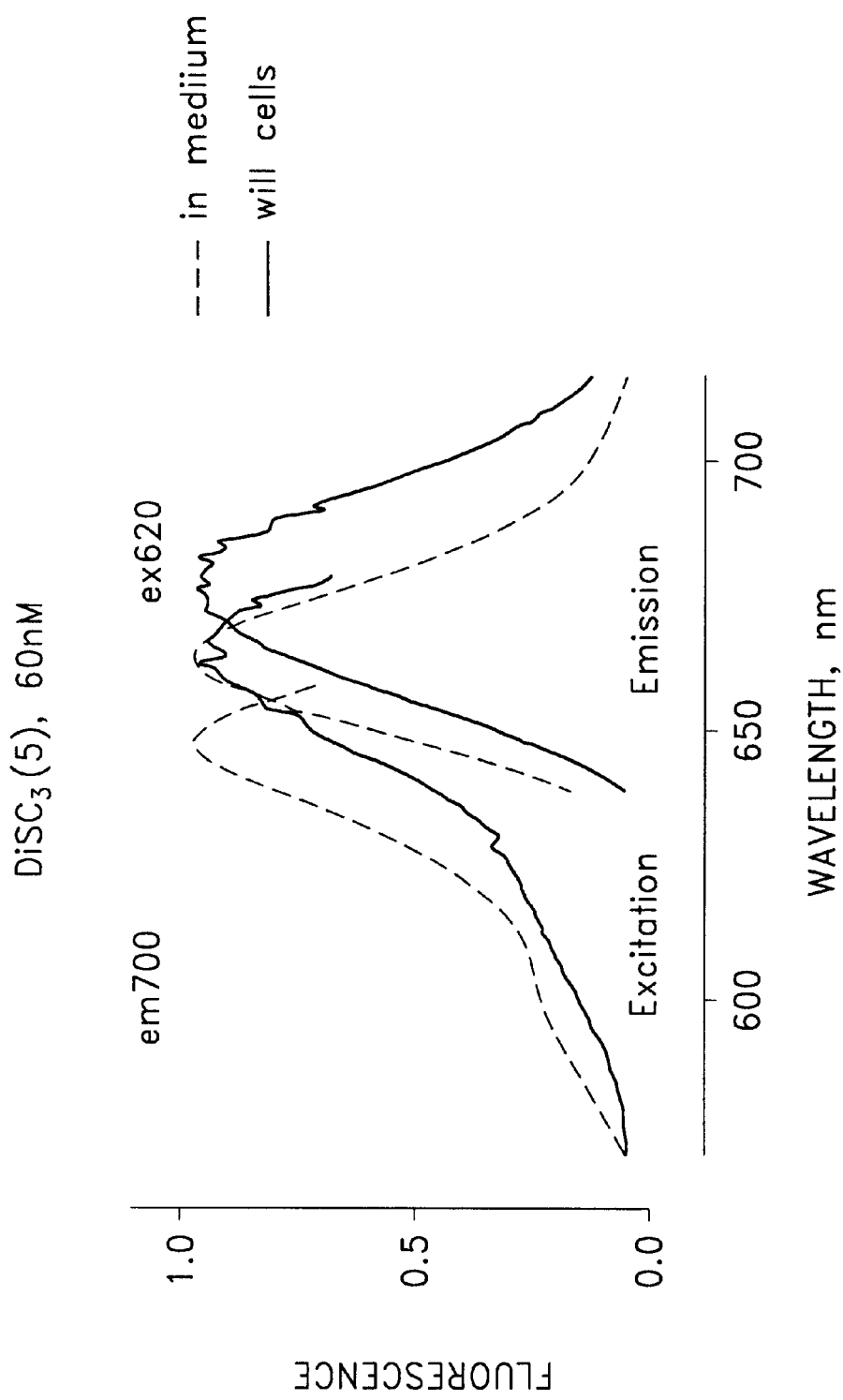
Figure 8F:
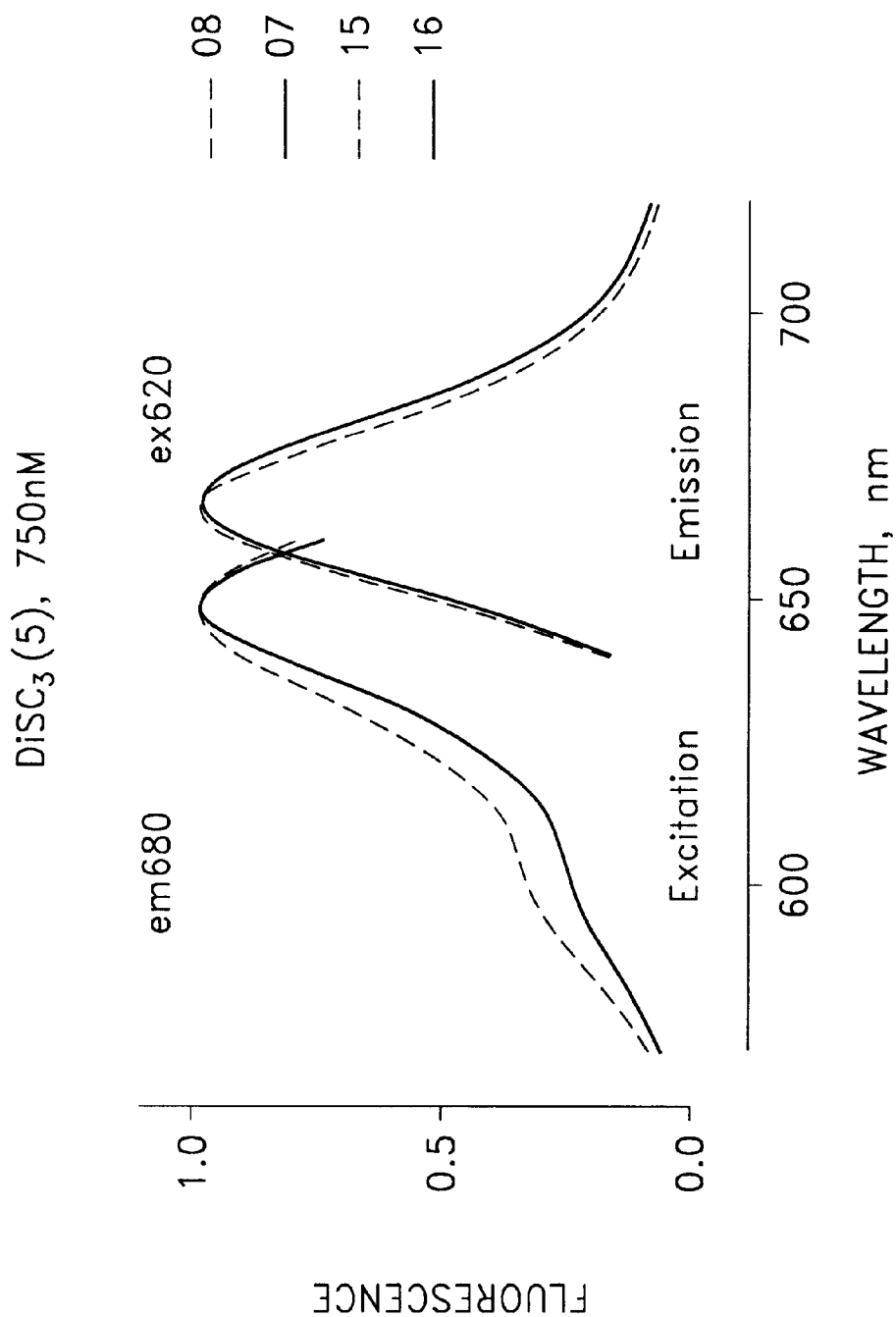

The cationic lipophilic dye $DISC_3(5)$ was used in this example. FIG. 8 shows a series of excitation and emission spectra of the dye in a medium without cells and in the presence of PC12 cells ($1.5 \times 10^5$ cells/ml). Cells were preincubated with the dye for 1 hour in a dark flask at different dye concentrations. After the incubation, aliquots of the cells (3 ml) were transferred in the fluorometer cuvette and the excitation and emission spectra were registered. For comparison, the dye spectra were registered in the same medium in the absence of cells. FIGS. 8a–c represent real recorded fluorescence traces and FIGS. 8d–f represent the same spectra normalized to their respective maxima. The normalization procedure usually simplifies recognition of spectral shifts. The addition of cells to the dye solution brings about significant quenching of the dye fluorescence [Bunting, et al., *Biophys J*. 56:979–993, 1989; Guillet et al., *J. Membr. Biol.* 59:1–11, 1981] (incorporated herein by reference). However, at low dye concentrations (up to 60 nM), there is a clear red spectral shift in the observable excitation maximum and emission maximum. As shown in FIG. 8f, at high dye concentrations the spectral shift is miniscule if at all. These data show that there are at least three forms of the dye that exist in the cell suspension, free "water" dye, with high quantum yield, an aggregated form of the dye, which is not fluorescent, and membrane bound dye with red shifted spectra. At low dye concentration, the main portion of the positively charged dye is concentrated into mitochondria and aggregates there because of its high concentration and limited solubility. A smaller portion of the dye is absorbed onto cell membranes and only a minor portion of the dye is in solution in free form. Under these conditions, the fluorescence is attributed predominantly to the membrane bound form of the dye. At higher dye concentrations, the limit of the dye uptake [Bunting et al., supra.; Guillet et al., supra.] is responsible for an increase in the free soluble dye concentration and, consequently, in concealing fluorescence of the membrane bound form of the dye. From the spectral data presented in FIG. 8, it can easily be appreciated by those skilled in the art that by choosing appropriate pairs of excitation and emission wavelengths one can simultaneously monitor fluorescence of "water" and membrane bound fractions of the dye.

Figure 9:
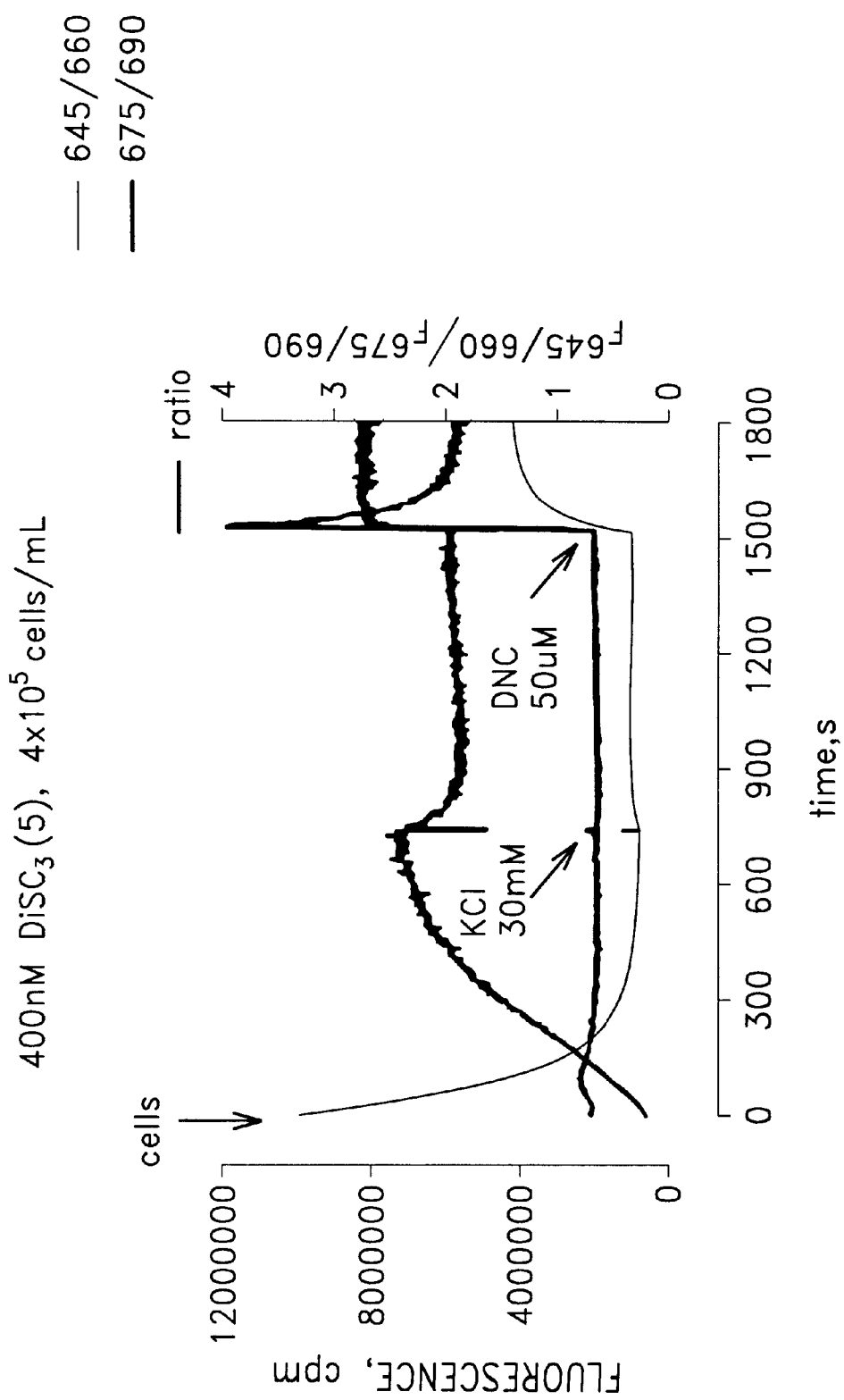
FIG. 9 shows kinetic changes in fluorescence intensity of $DiSC_3(5)$ upon PC 12 cell addition and after plasma membrane depolarization with KCl and mitochondria depolarization with the oxidative phosphorylation uncoupler 4,6-dinitro-o-cresol (DNC).

In the data presented in FIG. 9, the following wavelength pairs ($_{ex}/_{em}$) were chosen: 645 nm/660 nm for "water" dye (WD) and 675 nm/690 nm for membrane bound dye (MBD). After cells were added to the dye, the fluorescence of the WD ($645_{ex}/660_{em}$) diminished with time while the dye penetrated into and accumulated in the cell plasma and mitochondria. As it is clear from the trace, it is "water" dye fluorescence that was dramatically diminished upon the addition of the cells, with the membrane bound dye fluorescence staying practically at a constant level. In accordance with the Nernst equation, about 60 mV of plasma membrane potential assures a 10 fold increase in the free cytoplasm concentration of the dye relative to external media. A potential of about 180 mV across the inner mitochondria membrane creates a thousand fold increase in the mitochondria compartment relative to the cytoplasm concentration. When the dye concentration in the mitochondria reaches its solubility limit, the dye tends to aggregate with fluorescence quenching. Free dye concentrations in the media, in the cytoplasm and in mitochondria equilibrate with each other along with the dye aggregates and with the membrane bound dye when the ratio (about 1:10:10,000 in media/cytoplasm/mitochondria) of the free dye reaches values driven by respective membrane potentials. Upon addition of KCl, which depolarizes plasma membranes due to dissipating the trans-membrane potassium gradient, the fluorescence of "water" dye increases and fluorescence of the membrane bound dye decreases or stays constant so that the ratio between MBD and WD fluorescence decreases upon plasma membrane depolarization. When DNC, an uncoupler of mitochondrial oxidative phosphorylation, was added, fluorescence of both MBD and WD increased with the kinetic responses of the MBD being significantly faster than that of the WD. In this case, the ratio between fluorescence of the membrane bound and the "water" fractions increased momentarily and then returned to values characteristic of the depolarized cells.

Although the invention has been described in detail with reference to certain particular embodiments thereof, it will be understood that any variations and modifications apparent to those of skill in the art will still fall within the spirit and scope of the invention as provided by the following claims.

What is claimed is:

1. A method for identifying compounds having biological activity comprising:
   providing a first membrane penetrative dye having a first excitation energy and a first emission energy;
   providing a second membrane penetrative dye having a second excitation energy and a second emission energy, wherein said first emission energy is close to, or the same as, said second excitation energy;
   combining living cells with said first membrane penetrative dye and with said second membrane penetrative dye to form a test cell mixture;
   combining the test cell mixture with a test compound to form a test cell/compound mixture;
   placing said test cell/compound mixture into a detection zone;
   providing sufficient energy to said test cell/compound mixture to stimulate said first emission energy; and
   measuring the level of said second emission energy in said test cell/compound mixture, wherein the level of said second emission energy is indicative of said test compound having a biological activity.

2. The method of claim 1 wherein said test compound initiates a cellular response.

3. The method of claim 1 wherein said biological activity is a block of said cellular response.

4. The method of claim 1 wherein said first membrane penetrative dye is anionic and said second membrane penetrative dye is anionic.

5. The method of claim 1 wherein said cells are in a suspension.

6. The method of claim 1 wherein said cells are adhered to a substrate.

7. The method of claim 6 wherein said substrate is selected from the group consisting of beads, a microscope slide and a well of a multi-well plate.

8. The method of claim 1 wherein said test compound is in solution.

9. The method of claim 8 wherein said test compound solution comprises a standard compound having known biological effect.

10. The method of claim 9 wherein said standard compound is selected from the group consisting of ion channel openers, ion channel blockers, ion transporter blockers and ion pump blockers.

11. The method of claim 1 wherein said first membrane penetrable dye is a fluorescent lipophilic anion and said first excitation energy is between about 200 nm and 600 nm and said first emission energy is between about 300 nm and 700 nm.

12. The method of claim 1 wherein said second membrane penetrative dye is a fluorescent lipophilic anionic molecule and said second excitation energy is between about 300 nm and 700 nm and said second emission energy is between about 400 nm and 900 nm.

13. The method of claim 1, wherein said second membrane penetrative dye has a second excitation energy of between about 220 nm and 700 nm.

14. A method for identifying compounds having biological activity comprising:
   providing a membrane penetrative dye having a first excitation energy and a first emission energy, wherein said dye has a second excitation energy and a second emission energy when said dye is bound to intracellular hydrophobic surfaces of living cells;
   combining said living cells with said penetrative dye to form a test cell mixture;
   contacting said test cell mixture with said first excitation energy and measuring the level of said first emission energy;
   contacting said test cell mixture with said second excitation energy and measuring the level of said second emission energy;
   combining the test cell mixture with a test compound to form a test cell/compound mixture;
   contacting said test cell/compound mixture with said first excitation energy and measuring the level of said first emission energy;
   contacting said test cell/compound mixture with said second excitation energy and measuring the level of said second emission energy;
   comparing first emission energy from the test cell/standard mixture with the first emission energy from the test cell/compound mixture; and
   comparing second emission energy from the test cell/standard mixture with the second emission energy from the test cell/compound mixture.

15. The method of claim 14 wherein biological activity is exerted through modification of plasma membrane electric potential of said cells.

16. The method of claim 14 wherein biological activity is exerted through modification of mitochondrial membrane electric potential of said cells.

17. The method of claim 14 wherein said cells are in a suspension.

18. The method of claim 14 wherein said cells are adhered to a substrate.

19. The method of claim 18 wherein the substrate is selected from the group consisting of beads, a microscope slide and a well of a multi-well plate.

20. The method of claim 14 wherein said test compound is in a solution.

21. The method of claim 20 wherein said test compound solution comprises a standard compound having a known biological effect.

22. The method of claim 21 wherein said standard compound is selected from the group consisting of ion channel openers, ion channel blockers, ion transporter blockers and ion pump blockers.

23. The method of claim 21 wherein said test compound solution comprises a mixture of at least one said test compound and at least one said standard compound.

24. The method of claim 14 wherein said cellular response is measured by change in electric potential across a membrane.

25. The method of claim 24 wherein said membrane is the plasma membrane.

26. The method of claim 24, wherein said membrane is the mitochondrial membrane.

27. The method of claim 14 wherein said membrane penetrative dye is a fluorescent lipophilic cation chosen from a group of fluorescent dyes whose spectral characteristics are different when in solution and when bound to said cell membranes.

28. The method of claim 24 wherein said change in electric potential is measured by a change in fluorescence intensity of a membrane penetrative dye measured at least at two excitation and at least at two emission wavelengths.

29. The method of claim 28 wherein at least one excitation and at least one emission wavelength is chosen from the set of wavelengths characteristic of aqueous form of the dye.

30. The method of claim 28 wherein at least one excitation and at least one emission wavelength is chosen from the set of wavelengths characteristic of the membrane bound form of the dye.

31. The method of claim 28 wherein change in ratio of fluorescence intensity measured at the excitation and emission wavelengths characteristic of the unbound form of the dye to the fluorescence intensity measured at the excitation and emission wavelengths characteristic of the bound form of the dye is indicative of the combined electric potential of both the plasma membrane and the mitochondria membrane.

32. The method of claim 31 wherein a decrease in said ratio after combining said test cell mixture with said test compound is indicative of plasma membrane depolarization.

33. The method of claim 31 wherein an increase in said ratio after combining said test cell mixture with said test compound is indicative of mitochondrial membrane depolarization.

34. The method of claim 1, comprising combining the test cell mixture with a standard compound to form a test cell/standard mixture.

35. The method of claim 34 wherein said standard compound is selected from a group consisting of ion channel openers, ion channel blockers, ion transporter blockers and ion pump blockers.

36. The method of claim 34 wherein said standard compound initiates a cellular response.

37. The method of claim 34 wherein a change in a level of said second emission energy in said test cell/standard mixture compared to said test cell mixture indicates that said standard compound has said initiating effect on said cellular response.

38. The method of claim 1 wherein said test compound initiates a cellular response.

39. The method of claim 38 wherein a change in a level of said second emission energy in said test cell/compound mixture compared to said test cell mixture indicates that said test compound has said initiating effect on said cellular response.

40. The method of claim 34 wherein said test compound prevents a cellular response initiated with said standard compound.

41. The method of claim 40 wherein said cellular response, or said prevention of cellular response, is indicative of said biological activity of said test compound.

* * * * *